United States Patent [19]

Martel et al.

[11] Patent Number: 4,883,806

[45] Date of Patent: Nov. 28, 1989

[54] CERTAIN CYCLOPROPANEDICARBOXYLATES WITH AN UNSATURATED SIDE CHAIN HAVING INSECTICIDAL ACTIVITY

[75] Inventors: Jacques Martel, Bondy; Jean Tessier, Vincennes; Andre Teche, Paris, all of France

[73] Assignee: Roussel Uclaf, Paris, France

[21] Appl. No.: 100,284

[22] Filed: Sep. 23, 1987

Related U.S. Application Data

[60] Division of Ser. No. 756,396, Jul. 17, 1985, Pat. No. 4,732,903, which is a division of Ser. No. 550,081, Nov. 8, 1983, Pat. No. 4,542,142, which is a continuation-in-part of Ser. No. 279,076, Jun. 30, 1981, abandoned.

[30] Foreign Application Priority Data

Jul. 2, 1980 [FR] France ............................... 83 01344
Nov. 22, 1982 [FR] France ............................... 80 14722
Jan. 28, 1983 [FR] France ............................... 82 19515

[51] Int. Cl.$^4$ ................... C07D 209/52; A61K 31/40
[52] U.S. Cl. .................................. 514/417; 548/479; 560/124; 549/438; 546/300; 546/301
[58] Field of Search ...................... 514/417; 548/479

[56] References Cited

U.S. PATENT DOCUMENTS 4,489,093 12/1984 Martel et al. .................... 514/417
4,607,026 8/1986 Tessier et al. .................... 514/80

*Primary Examiner*—Alan L. Rotman
*Attorney, Agent, or Firm*—Bierman & Muserlian

[57] ABSTRACT

Novel isomers and mixtures thereof of cyclopropane carboxylic acid derivatives with a 3-unsaturated side chain of the formula

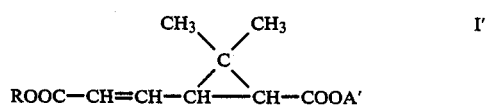

wherein A' is selected from the group consisting of (1) alkyl of 1 to 18 carbon atoms, (2) benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms, methylenedioxy or halogen,

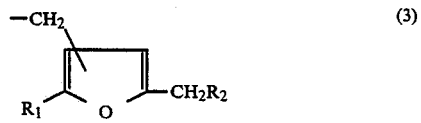

wherein $R_1$ is selected from the group consisting of hydrogen and methyl and $R_2$ is selected from the group consisting of $-CH_2-C\equiv CH$ and monocyclic aryl,

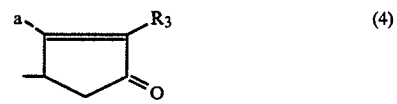

wherein a is selected from the group consisting of hydrogen and methyl and $R_3$ is an aliphatic group of 2 to 6 carbon atoms containing at least one carbon-carbon unsaturation

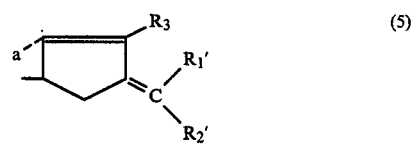

wherein a and and $R_3$ have the above definition and $R_1'$ and $R_2'$ are individually selected from the group consisting of hydrogen, halogen, alkyl of 1 to 6 carbon atoms, aryl of 6 to 10 carbon atoms, cyano and alkoxy carbonyl of 2 to 5 carbon atoms, (6)

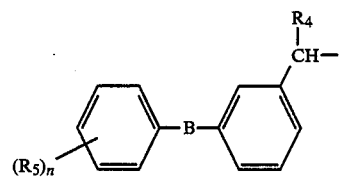

wherein B is selected from the group consisting of

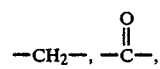

$-O-$ and $-S-$, $R_4$ is selected from the group consisting of hydrogen, $-CH_3$, $-C\equiv N-CONH_2$, $-CSNH_2$ and $-C\equiv CH$, n is an integer form 0, 1 or 2 and $R_5$ is selected from the group consisting of halogen and $-CH_3$

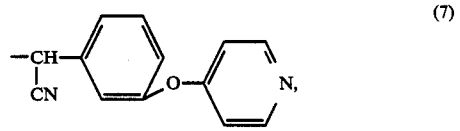

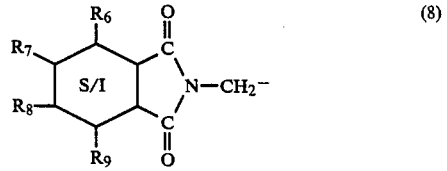

wherein $R_6$, $R_7$, $R_8$ and $R_9$ are selected from the group (Abstract continued on next page.)

consisting of hydrogen, chlorine and methyl and S/I symbolizes an aromatic ring or dihydro or tetrahydro ring,

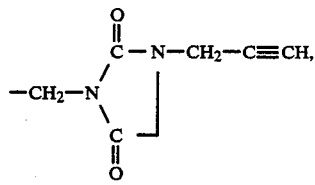 (9)

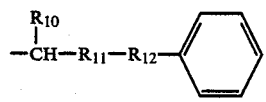 (10)

wherein $R_{10}$ is selected from the group consisting of hydrogen and —CN, $R_{12}$ is selected from the group consisting of —CH$_2$— and —O— and $R_{11}$ is selected from the group consisting of thiazolyl and thiadiazolyl with the bond the bond to

being in anyone of the positions, $R_{12}$ being bonded to $R_{11}$ by the carbon atom included between a sulfur atom and a nitrogen atom, (11)

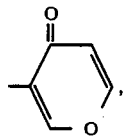 (12)

wherein $R_{13}$ is selected from the group consisting of hydrogen and —CN

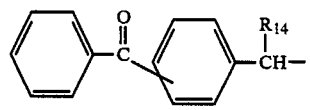 (13)

wherein $R_{13}$ has the above definition and the benzoyl is in the 3- or 4-position;

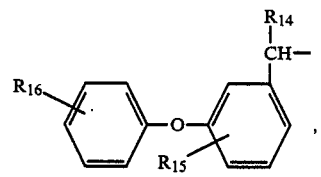 (14)

wherein $R_{14}$ is; selected from the group consisting of hydrogen, methyl, ethynyl and —CN and $R_{15}$ and $R_{16}$ are individually selected from the group consisting of hydrogen, bromine and fluorine and

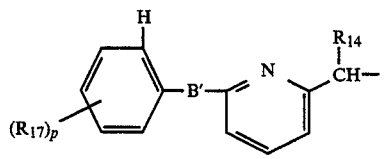 (15)

wherein $R_{14}$ has the above definition, p is 0, 1 or 2, each $R_{17}$ is selected from the group consisting of alkyl of 1 to 4 carbon atoms, alkoxy of 1 to 4 carbon atoms, alkylthio of 1 to 4 carbon atoms, alkylsulfonyl of 1 to 4 carbon atoms, —CF$_3$ 3,4-methylenedioxy, chlorine, bromine and fluorine, B is selected from the group consisting of —O— and —S— and R is selected from the group consisting of alkyl of 1 to 18 carbon atoms substituted with one or more, optionally different functional groups, aryl of 6 to 14 carbon atoms optionally substituted with one or more optionally different functional groups, the double bond having Z or E geometry having insecticidal and nematocidal activity as well as plant and animal acaricidal activity and their preparation.

3 Claims, No Drawings

CERTAIN CYCLOPROPANEDICARBOXYLATES WITH AN UNSATURATED SIDE CHAIN HAVING INSECTICIDAL ACTIVITY

PRIOR APPLICATION

This application is a division of U.S. patent application Ser. No. 756,396 filed July 17, 1985 U.S. Pat. No. 4,732,903, which is a division of U.S. patent application Ser. No. 550,081 filed Nov. 8, 1983 which is a continuation-in-part of our copending, commonly assigned U.S. patent application Ser. No. 279,076 filed June 30, 1981.

STATE OF THE ART

Certain derivatives of cyclopropane carboxylic acid derivatives are known having in the 3-position the group ROOC—CH=CH— having essentially E geometry. Examples of such prior art are French Pat. No. 2,185,612 as well as J. Chem. Soc., Perkin I (1974), p. 2470 and Pest. Sci., Vol. 7 (1976), p. 499. The processes used to prepare these derivatives lead almost exclusively to the E geometry (for example Arg. Biol. Chem. Vol. 34 (1970) p. 1119). Furthermore, for these compounds with the side chain geometry in the E state, it has not been possible to make evident any remarkable properties. The French Pat. Nos. 2,418,218 and 2,143,820 also describe compounds substituted in the 3-position by the group ROOC—CH=CH—.

OBJECTS OF THE INVENTION

It is an object of the invention to provide the novel Z and E isomers of the compounds of formula I' as well as a novel process and novel intermediates for their preparation.

It is another object of the invention to provide novel pesticidal compositions and a novel method of killing insects, nematodes and vegetable and animal acariens.

It is a further object of the invention to provide novel compositions and method of combatting scabies and to provide anthelmintic activity.

These and other objects and advantages of the invention will become obvious from the following detailed description.

THE INVENTION

The novel compounds of the invention are selected from the group consisting of isomers and mixtures thereof of cyclopropane carboxylic acid derivatives with a 3-unsaturated side chain of the formula

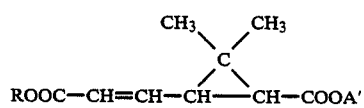

wherein A' is selected from the group consisting of (1) alkyl of 1 to 18 carbon atoms, (2) benzyl optionally substituted with at least one member of the group consisting of alkyl of 1 to 4 carbon atoms, alkenyl of 2 to 6 carbon atoms, alkenyloxy of 2 to 6 carbon atoms, alkadienyl of 4 to 8 carbon atoms methylenedioxy and halogens,

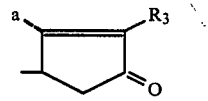

wherein R is selected from the group consisting of hydrogen and methyl and $R_2$ is selected from the group consisting of —$CH_2$—C≡CH and monocyclic aryl,

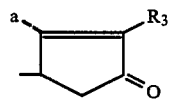

wherein a is selected from the group consisting of hydrogen and methyl and $R_3$ is an aliphatic group of 2 to 6 carbon atoms containing at least carbon-carbon unsaturation,

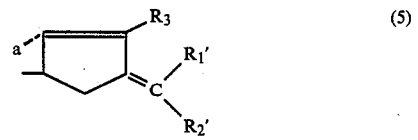

wherein a and and $R_3$ have the above definition and $R_1'$ and $R_2'$ are individually selected from the group consisting of hydrogen, halogen, alkyl of 1 to 6 carbon atoms, aryl of 6 to 10 carbon atoms, cyano and alkoxy carbonyl of 2 to 5 carbon atoms, (6)

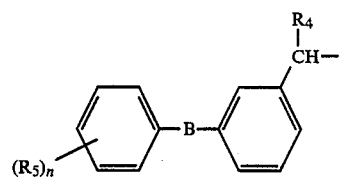

wherein B is selected from the group consisting of

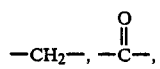

—O— and —S—, $R_4$ is selected from the group consisting of hydrogen, C≡N, —$CH_3$, —$CONH_2$, —$CSNH_2$ and —C≡CH, n is an integer from 0, 1 or 2 and $R_5$ is selected from the group consisting of halogen and —$CH_3$

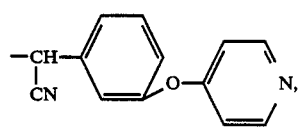

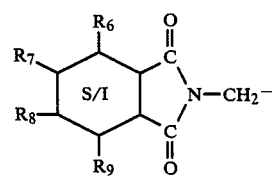

wherein $R_6$, $R_7$, $R_8$ and $R_9$ are selected from the group consisting of hydrogen, chlorine and methyl and S/I symbolizes an aromatic ring or dihydro or tetrahydro ring,

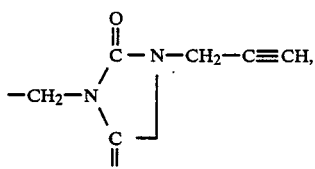 (9)

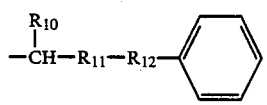 (10)

wherein $R_{10}$ is selected from the group consisting of hydrogen and —CN, $R_{12}$ is selected from the group consisting of —$CH_2$— and —O— and $R_{11}$ is selected from the group consisting of thiazolyl and thiadiazolyl with the bond to

being in any one of the positions, $R_{12}$ being bonded to $R_{11}$ by the carbon atom included between a sulfur atom and a nitrogen atom,

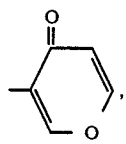 (11)

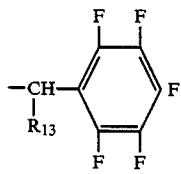 (12)

wherein $R_{13}$ is selected from the group consisting of hydrogen and —CN,

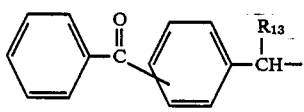 (13)

wherein $R_{13}$ has the above definition and the benzoyl is in the 3- or 4-position,

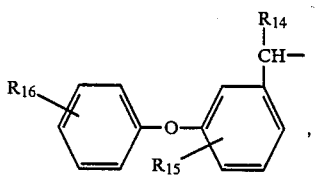 (14)

wherein $R_{14}$ is selected from the group consisting of hydrogen, methyl, ethynyl and —CN and $R_{15}$ and $R_{16}$ are individually selected from the group consisting of hydrogen, bromine and fluorine and

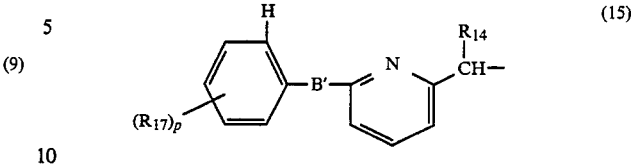 (15)

wherein $R_{14}$ has the above definition, p is 0, 1 or 2 each $R_{17}$ is selected from the group consisting of alkyl of 1 to 4 carbon atoms, alkoxy of 1 to 4 carbon atoms, alkylthio of 1 to 4 carbon atoms, alkylsulfonyl of 1 to 4 carbon atoms, —$CF_3$, 3,4-methylenedioxy, chlorine, bromine and fluorine, B is selected from the group consisting of —O— and —S— and R is selected from the group consisting of alkyl of 1 to 18 carbon atoms substituted with one or more, optionally different functional groups, aryl of 6 to 14 carbon atoms optionally substituted with one or more optionally different functional groups, or a heterocyclic radical optionally substituted with one or more optionally different functional groups the double bond having Z or E geometry.

An example of $R_2$ as monocyclic aryl is 5-benzyl-3-furyl-methyl and examples of $R_3$ are —$CH_2$—CH=$CH_2$, —$CH_2$—CH=CH—$CH_3$, —$CH_2$—CH=CH—$CH_2$—$CH_3$ and —$CH_2$—CH=CH—CH=$CH_2$—. Examples of substituent (6) are 3-phenoxy-benzyl, α-cyano 3-phenoxy-benzyl, α-ethynyl-3-phenoxy-benzyl, 3-benzoyl-benzyl, 1-(3-phenoxyphenyl)-ethyl and α-thioamido-3-phenoxy benzyl.

The compounds of formula I' exist in isomeric forms due to the presence of asymmetric carbon atoms in the 1- and 3-positions of the ring, to other asymmetric centers in the alcohol portions thereof and to the configuration of the double bond in the side chain in the 3-position.

Examples of A' are alkyl such as methyl, ethyl, n-propyl, isopropyl, isobutyl, tert.-butyl and n-butyl; benzyl optionally substituted with at least one alkyl such as methyl or ethyl; benzyl optionally substituted with at least one alkenyl such as vinyl, allyl, 2-methylallyl and isobutenyl; and benzyl substituted with at least one alkenyloxy such as vinyloxy, allyloxy, 2-methylallyloxy and isobutenyloxy; and benzyl substituted with at least one halogen such as chlorine bromine or fluorine.

Examples of R substituted with one or more functional groups are preferably alkyl of 1 to 8 carbon atoms such as methyl, ethyl, propyl, isopropyl, n-butyl, isobutyl or tert. butyl substituted with at least one member of the groups consisting of halogen, —OH, —SH, —OR' and —SR' and R' is selected from the group consisting of alkyl of 1 to 8 carbon atoms $$-NO_2, -CN, -SO_3H, -PO_4H_2, -N\begin{matrix}R''\\ \diagup\\ \diagdown\\ R'''\end{matrix},$$

$$-\overset{O}{\underset{\|}{C}}-Alk_1, -SO_2Alk_2 \text{ and}$$

$SO_3AlK_3$, R'' and R''' are individually selected from the group consisting of hydrogen and alkyl of 1 to 8 carbon atoms and $AlK_1$, $AlK_2$ and $AlK_3$ are alkyl of 1 to 18 carbon atoms.

R may also be alkyl substituted with an aryl group such as benzyl or phenethyl optionally substituted with at least one member of the group consisting of —OH, alkyl and alkoxy of 1 to 8 carbon atoms, —CF$_3$, —OCF$_3$, —SCF$_3$ and $$\begin{array}{c} O \\ \diagdown \\ CH_2(G). \\ \diagup \\ O \end{array}$$

R may also be alkyl substituted on two adjacent carbon atoms with the group $$\begin{array}{c} -O \\ \diagdown \\ CH_2 \, (G_1) \\ \diagup \\ -O \end{array}$$

or substituted with $$-O-\!\!\!\bigcirc\!\!\!\!-O$$

When R is an alkyl radical substituted by one or more functional groups, the preferred examples of R are (1) —(CH$_2$)$_n$—CHal$_3$ wherein n is an integer from 1 to 8 and Hal is a halogen, such as —CH$_2$—CCl$_3$, —CH$_2$—CF$_3$, —CH$_2$—CH$_2$—CCl$_3$ or —CH$_2$—CH$_2$—CF$_3$, (2) —(CH$_2$)$_{n1}$—CHHal$_2$ wherein n$_1$ is 0 to 8 and Hal is halogen such as —CH$_2$—CHCl$_2$, —CH$_2$—CHF$_2$ and —CHF$_2$, (3) —(CH$_2$)$_n$—CH$_2$Hal wherein Hal and n have the above definitions, such as —CH$_2$—CH$_2$—Cl or —CH$_2$—CH$_2$F, (4) —C—(CHal$_3$)$_3$ wherein Hal is a halogen, such as —C(CF$_3$)$_3$ or $-\overset{\overset{CF_3}{|}}{\underset{\underset{CCl_3}{|}}{C}}-CF_3$ (5) $-\overset{\overset{CF_3}{|}}{\underset{\underset{CF_3}{|}}{C}}-CH_3$, $-\overset{\overset{CH_3}{|}}{\underset{\underset{CH_3}{|}}{C}}-CF_3$, $-\overset{\overset{CF_3}{|}}{\underset{\underset{CH_2-CH_3}{|}}{C}}-CH_3$, (6) $-\overset{\overset{CF_3}{|}}{\underset{\underset{H}{|}}{C}}-CH_3$, $-\overset{\overset{CF_3}{|}}{\underset{}{CH}}-CF_3$, (7) $-\overset{\overset{CH_3}{|}}{\underset{\underset{CH_3}{|}}{C}}-CN$, $-\overset{\overset{CH_3}{|}}{\underset{}{CH}}-CN$, —(CH$_2$)$_n$—CN wherein n is 1 to 8, (8) $-\overset{\overset{CHal_3}{|}}{\underset{}{CH}}-CN$ wherein Hal is a halogen, such as $-\overset{\overset{CCl_3}{|}}{\underset{}{CH}}-CN$, (9) (CH$_2$)$_n$—OR' wherein n has the above definition and R' is hydrogen or branched or linear alkyl of 1 to 8 carbon atoms such —CH$_2$—OCH$_3$, —CH$_2$—CH$_2$—OCH$_3$, —CH$_2$—CH$_2$—O—CH$_2$—CH$_3$ or —CH$_2$—CH$_2$—OH, (10)

$$-(CH_2)_n-N\diagup^{R''}_{\diagdown R'''}$$

wherein n is 1 to 8 and R'' and R''' are individually hydrogen or branched or linear alkyl such as —CH$_2$—CH$_2$—NH—CH$_3$, $-CH_2-CH_2-N\diagup^{CH_3}_{\diagdown CH_3}^{CH_3}$ or $-CH_2-CH_2-\overset{\overset{CH_3}{|}}{\underset{}{N}}-CH_2-CH_3$,

(11) $-(CH_2)_n-\overset{}{\underset{O\diagdown}{CH}}\!\!\!\!-\!\!\!\!\overset{}{\underset{\diagup O}{CH_2}}$
$\phantom{(11) -(CH_2)_n-CH}\underset{CH_3\phantom{X}CH_3}{C}$ wherein n is 1 to 8 such as $-(CH_2)_n-\overset{}{\underset{O\diagdown}{CH}}\!\!\!\!-\!\!\!\!\overset{}{\underset{\diagup O}{CH_2}}$, (12) $-(CH_2)_n-\overset{\overset{}{\underset{OH}{|}}}{CH}-\overset{\overset{}{\underset{OH}{|}}}{CH_2}$
$\phantom{-(CH_2)_n-CH}\underset{CH_3\phantom{X}CH_3}{C}$ wherein n is 1 to 8 such as —CH$_2$—$\overset{\overset{}{\underset{OH}{|}}}{CH}$—CH$_2$—OH, (13) —(CH$_2$)$_n$—O—$\!\!\!\bigcirc\!\!\!\!$$^O$ wherein n is 1 to 8 such as —CH$_2$—O—$\!\!\!\bigcirc\!\!\!\!$$^O$ or —CH$_2$—CH$_2$—O—$\!\!\!\bigcirc\!\!\!\!$$^O$, (14) —(CH$_2$)$_n$—$\!\!\!\bigcirc\!\!\!\!$ wherein n is 1 to 8 such as benzyl or phenethyl and

(15) —(CH$_2$)$_n$—$\!\!\!\bigcirc\!\!\!\!$$^{O-CH_2}_{\diagdown O}$ wherein n is 1 to 8 such as

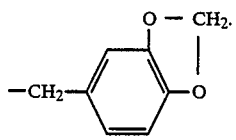

When R is an optionally substituted aryl, preferred examples are phenyl optionally substituted with at least one member of the group consisting of —OH, alkyl and alkoxy of 1 to 8 carbon atoms, —CF$_3$, —OCF$_3$ and —SCF$_3$. Example of R as heterocycles are pyridinyl, furanyl, thiophenyl, oxazolyl and thiazolyl.

Among the preferred compounds of formula I' are those of the formula

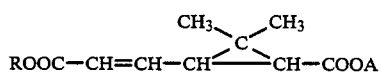   I wherein A is selected from the group consisting of (1) alkyl of 1 to 18 carbon atoms, (2) benzyl optionally substituted as before,

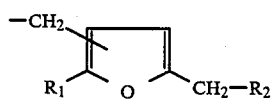   (3)

wherein R$_1$ and R$_2$ have the above definition,

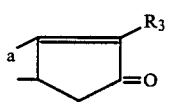   (4)

wherein R$_3$ and a have the above definition,

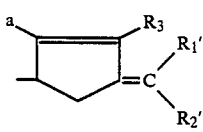   (5)

wherein a, R$_3$, R$_1'$ and R$_2'$ have the above definition,

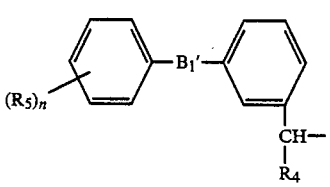   (6)

wherein R$_4$, and n have the above definitions, R$_5$ is selected from the group consisting of methyl and chlorine and B'$_1$ is selected from the group consisting of

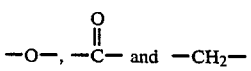   (7)

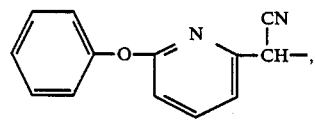   (8)

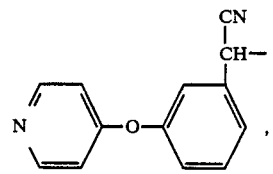   (9)

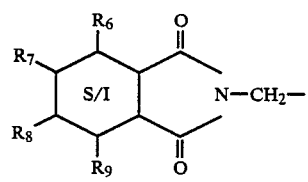

wherein S/I, R$_6$, R$_7$, R$_8$ and R$_9$ have the above definitions and

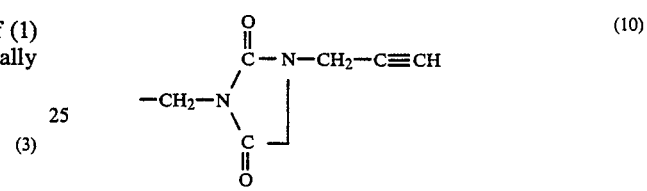   (10)

and R has the above definition. R is preferably 3-phenoxy-benzyl, α-cyano-3-phenoxy-benzyl or 60 -ethynyl-3-phenoxy-benzyl.

The preferred compounds of formula I or I' have the cyclopropanecarboxylic acid in the 1R, cis or 1R, trans structure and most preferably have the 1R, cis structure.

The preferred compounds of formula I' have the double bond with the geometry Z.

Among the preferred compounds of formula I' are those wherein A' is α-cyano-3-phenoxy-benzyl in its S, R or R,S forms and those wherein A' is 2-methyl-4-oxo-3-(2-propenyl)-2-cyclopenten-1-yl in its R,S or RS forms, those wherein R is alkyl of 1 to 18 carbon atoms substituted with at least one functional group, especially those substituted with at least one halogen such as fluorine, most especially —CH$_2$—CF$_3$.

The most preferred compounds of formula I' are those of Examples 1,2,23,26,29,30 and 35.

The novel process of the invention for the preparation of the compounds of formula I' comprises reacting a compound of the formula

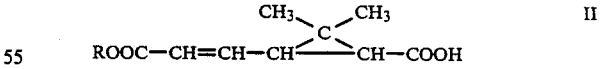   II wherein R has the above definition or a functional derivative thereof with an alcohol of the formula A'—OH III wherein A' has the above definition to obtain the corresponding compound of formula I'.

The preferred functional acid derivative is the acid chloride. The esterification may be effected by known methods such as reacting the acid of the formula II with the alcohol of formula III in the presence of dicyclohexylcarbodiimide or diisopropylcarbodiimide.

The compounds of formula II may be prepared by reacting in an organic solvent a compound of the formula $$\underset{HC-CH\overset{\displaystyle CH_3\diagdown\diagup CH_3}{\overset{\displaystyle C}{\diagup\diagdown}}CH-COOH}{\overset{O}{\underset{\|}{}}} \quad B_1$$

in its trans form or the form of a cis lactone with a compound of the formula $$\underset{RO-C-CH-P\equiv(\Phi)_3}{\overset{O}{\underset{\|}{}}\ \ ^{(-)\ \ (+)}} $$

(called $B_2$) wherein R has the above definition to obtain the corresponding acid of formula II in the form a mixture of its E and Z isomers which may be separated into its individual isomers, if desired, by known methods. The preferred organic solvent is selected from the group consisting of ether, dimethylsulfoxide, dimethylformamide, tetrahydrofuran, dimethoxyethane, alkanols, monoethyl ether of diethyleneglycol and the diethyl ether of diethyleneglycol.

The compound of formula $B_2$ may be prepared by reaction of a compound of the formula $$(\Phi)_3 \overset{(+)}{\equiv} P-CH_2-COOR.Hal^{(-)}$$

wherein $Hal^-$ is a halide anion with a strong base such as alkali metal hydrides, alkali metal amides, alkali metal alcoholate or alkyllithiums.

The compounds of formula II may also be prepared by reacting a compound of the formula $$\underset{Hal}{\overset{Hal}{\diagdown}}C=CH-CH\overset{\displaystyle CH_3\diagdown\diagup CH_3}{\overset{\displaystyle C}{\diagup\diagdown}}CH-COOAlK \quad IV$$

wherein Hal is a halogen and AlK is alkyl of 1 to 20 carbon atoms in a first step with an alkaline agent capable of taking off the halogen atom and in a second step ether (a) with an agent capable of introducing a carboxylic acid group to obtain a compound of the formula $$\underset{HO-C-C\equiv C-CH\overset{\displaystyle CH_3\diagdown\diagup CH_3}{\overset{\displaystyle C}{\diagup\diagdown}}CH-COOAlK}{\overset{O}{\underset{\|}{}}} \quad V$$

and reacting the latter with an esterification agent to obtain a compound of the formula $$\underset{RO-C-C\equiv C-CH\overset{\displaystyle CH_3\diagdown\diagup CH_3}{\overset{\displaystyle C}{\diagup\diagdown}}CH-COOAlK}{\overset{O}{\underset{\|}{}}} \quad VI$$

wherein R has the above definition or (b) with an alkyl haloformate of the formula $$\underset{R-O-C-Hal}{\overset{O}{\underset{\|}{}}} \quad V'$$

wherein Hal is a halogen to obtain directly the corresponding compound of formula VI, reacting the compound of formula VI with a careful hydrogenation agent to obtain a compound of the formula $$\underset{RO-C-CH=CH-CH\overset{\displaystyle CH_3\diagdown\diagup CH_3}{\overset{\displaystyle C}{\diagup\diagdown}}CH-COOAlK}{\overset{O}{\underset{\|}{}}} \quad VII$$

with the double bond having the Z geometry, subjecting the latter to an acid hydrolysis agent capable of selectively cleaving the ester function on the 1-position to obtain the compound of formula II.

In a preferred mode of the said process, the Hal is bromine or chlorine and AlK is tert.-butyl. The alkaline agent capable of removing the vinyl halogens is butyllithium and the agent capable of introducing a carboxyl group is carbon dioxide. The preferred careful hydrogenation agent is hydrogen in the presence of a catalyst such as palladium in the presence of traces of quinoline. The selective acid hydrolysis agent is p-toluene sulfonic acid. In an obvious variation of the said process, the compound of formula V may be subjected to a careful hydrogenation agent and treated in a second step with a reducing agent.

In a variation of the process of the invention, a compound of formula V is treated with a careful hydrogenation agent to obtain a compound of the formula $$HOOC-CH=CH-CH\overset{\displaystyle CH_3\diagdown\diagup CH_3}{\overset{\displaystyle C}{\diagup\diagdown}}CH-COOAlK \quad VIII$$

with the double bond having the Z geometry which is then reacted with an esterification agent to obtain the corresponding compound of formula VII which is then reacted as described above.

In a variation of this process these above steps may be reversed.

In another embodiment of the process of the invention, a compound of formula VI is reacted with an acid hydrolysis agent capable of selectively cleaving the 1-ester function of the cyclopropane ring to obtain a compound of the formula $$\underset{ROC-C\equiv C-CH\overset{\displaystyle CH_3\diagdown\diagup CH_3}{\overset{\displaystyle C}{\diagup\diagdown}}CH-COOH}{\overset{O}{\underset{\|}{}}} \quad IX$$

which compound or optionnally a functional derivative of the latter is then either reacted with an alcohol of formula III to obtain a compound of the formula $$\underset{ROC-C\equiv C-CH\overset{\displaystyle CH_3\diagdown\diagup CH_3}{\overset{\displaystyle C}{\diagup\diagdown}}CH-COOA'}{\overset{O}{\underset{\|}{}}} \quad X$$

wherein R and A' have the above definition and subjecting the latter to a careful hydrogenation agent to obtain the corresponding compound of formula I' or subjecting the compound of formula IX to a careful hydrogenation agent to obtain the corresponding compound or formula II with the double bond having the Z geometry and reacting this compound or optionally a functional derivative of the latter with a compound of formula III to obtain the corresponding compound of formula I'. The preferred operating conditions are the same as discussed above for the various steps.

Another process for the preparation of a compound of formula I' comprises reacting a compound of the formula

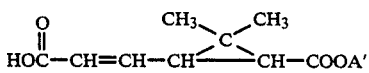

with the double bond having the Z geometry with an esterification agent to obtain the corresponding compound of formula I'. Preferably, the esterification is effected with a functional derivative of the alcohol such as the N,N'-diisopropylurea derivative of the formula

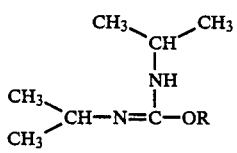

The process of the invention for the preparation of the compound of formula XI comprises reacting an acid of formula V when AlK is alkyl of 1 to 8 carbon atoms with 2,2,2,-trichloroethanol to obtain a compound of the formula

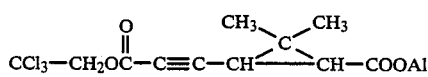

reacting the latter with an acid hydrolysis agent to obtain a compound of the formula

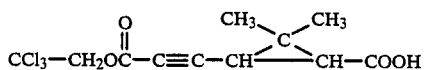

reacting the latter with an alcohol of formula III to obtain a compound of the formula

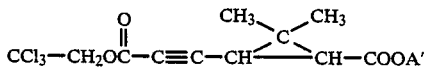

subjecting the latter to a cleavage agent capable of taking the ester group off the acetylenic chain to obtain a compound of the formula

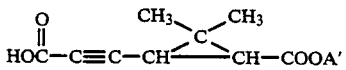

and reacting the latter with a careful hydrogenation agent to obtain the compound of formula XI.

Preferably, the AlK group of the compound of formula V is tert.-butyl and the acid hydrolysis agent is p-toluene sulfonic acid. The esterification of the compound of formula XIII is effected by reaction of the alcohol of formula III in the presence of dicyclohexylcarbodiimide or diisopropylcarbodiimide. The cleavage of the ester of formula XIV is preferably effected with a powdered metal such as zinc in an acid medium and the careful hydrogenation is effected with hydrogen in the presence of a catalyst such as palladium in the presence of traces of quinoline. The esterification and the hydrogenation steps may be reversed.

In a further embodiment of a process of the invention to produce a compound of formula I', a compound of the formula

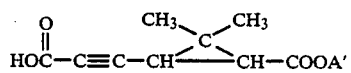

wherein A' has the above definition is reacted with an esterification agent to obtain the corresponding compound of formula X which is then reacted with a careful hydrogenation agent to obtain the corresponding compound of formula I'. The preferred reaction conditions are the same as discussed above for analogous reactions.

To prepare a compound of formula I' wherein R is alkyl substituted with at least one hydroxy group, a compound of formula I' wherein R is alkyl substituted with at least one protected hydroxy group such as dioxolanyl or tetrahydropyranyl is subjected to hydrolysis with an acid hydrolysis agent such as hydrochloric acid or p-toluenesulfonic acid.

The majority of the processes described above lea to the compounds of formula I' with the double bond having the Z geometry and the process results in excellent yields as can be seen from the specific examples.

The compounds of formulae II, VI, VII, IX and X are novel intermediates and are a portion of the invention as well.

The novel pesticidal compositions of the invention are comprised of a pesticidally effective amount of at least one compound of formula I' and an inert carrier. The compositions are useful to combat pests such as parasites of vegetables and of warm-blooded animals as well as domestic parasites and are particularly useful to combat insects, nematodes and parasitic acariens which attack warm-blooded animals and vegetables.

The compositions of the invention are particularly useful to combat insects in the agricultural field, for example to control aphides and larvae of lepidoptera and coleoptera and are usually used at a dose of 10 to 300 g of the compound of formula I' per hectare. The compositions are also useful to combat insects in the premises for example to combat flies, mosquitoes and beetles.

Certain of the compounds of formula I' possess an excellent lethal power and a very good knock-down power and the product of Example 1 is particularly remarkable on this point. The products of formula I' have the advantages of being very photostable and not being toxic to mammals. The various properties of the compounds of formula I' correspond perfectly to those required for modern agrochemical use permitting the protection of crops without damage to the environment.

The pesticidal compositions of the invention are useful to combat vegetable parasitic acariens and nematodes as well as to combat animal parasitic acariens such as ticks, especially ticks of Boophilus species, Hyalomnia species, Amblyomnia species and Rhipicephalus species and to combat all sorts of scabies such as sarcoptic scabies, psoroptic scabies and chorioptic scabies.

The invention also includes compositions intended to combat parasites of warm-blooded animals, parasites of premises and parasites of vegetables containing at least one compound of formula I'.

The invention particularly includes insecticidal compositions containing as active principle, at least one compound of formula I'.

Among the preferred insecticidal compositions of the invention are those wherein the active ingredient is selected from the group consisting of (S)α-cyano-3- phenoxy-benzyl (1R,cis,ΔZ) 2,2-dimethyl-3-[3-(2,2,2-trifluoroethoxy)-3-oxo-1-propenyl]-cyclopropane-carboxylate, (S)α-cyano-3-phenoxy-benzyl (1R,cis,ΔZ) 2,2-dimethyl-3-[3-{2-(1,1,1,3,3,3,-hexafluoro}-propoxy-3-oxo-1-propenyl]-cyclopropane-carboxylate, (R)α-ethynyl-3-phenoxy-benzyl (1R,cis,ΔZ) 2,2-dimethyl-3-[3-(2,2,2-trifluoroethoxy)-3-oxo-1-propenyl]-cyclopropane-carboxylate, (R,S) cyano-6-phenoxy-2-pyridyl-methyl (1R,cisΔZ) 2,2-dimethyl-3-[3-(2,2,2-trifluoroethoxy)-3-oxo-1-propenyl)-cyclopropane-carboxylate, (S)α-cyano-3-phenoxy-benzyl (1R,cis,αZ) 2,2-dimethyl-3-[3-(2-fluoroethoxy)-3-oxo-1-propenyl]-cyclopropane-carboxylate, (3-propargyl-2,5-dioxo-imidazolidinyl)-methyl (1R,cis,αZ) 2,2-dimethyl-3-[3-(2,2,2-trifluoroethoxy)-3-oxo-1-propenyl-cyclopropane-carboxylate and (1S) 2-methyl-4-oxo-3-(2-propenyl-2-cyclopenten-1-yl (1R,cis,αZ) 2,2-dimethyl-3-[3-(2,2,2-trifluoroethoxy)-3-oxo-1-propenyl]-cyclopropane-carboxylate.

For the compositions intended for premises or agricultural use, the compositions may also contain one or more other pesticidal agents. The compositions may be in the form of powders, granules, suspensions, emulsions, solutions, aerosol solutions, combustible bands, baits and other preparations classically used for compounds of this type.

Besides the active ingredient, the compositions generally contain a vehicle and/or a nonionic surface active agent to ensure a uniform dispersion of the substances in the mixture. The vehicle used may be a liquid such as water, alcohol, hydrocarbons or other organic solvents or a mineral, animal or vegetable oil or a powder such as talc, clays, silicates or Kieselguhr or a combustible solid. The insecticidal compositions usually contain 0.005 to 10% by weight of the compounds of formula I'.

In an advantageous operation for use in premises, the compositions are in the form of fumigants. These compositions advantageously have for their inactive portion a combustible serpentine or coil base or an incombustible fibrous substrate. In the latter case, the fumigant obtained after incorporation of the active ingredient of formula I' is placed in a heating apparatus such as an electromosquitoe destroyer. The usual active dose in this case is 0.03 to 95% by weight, preferably.

In the case of a serpentine insecticide, the inert support may be made, for example, of pyrethrum marc, Tabu powder (or Machilus Thumbergii leaf powder), powder of pyrethrum stems, cedar needle powder, sawdust such as pine sawdust starch and powder of coconut shells. The active dose in this case is preferably 0.03 to 1% by weight.

The compositions of the invention for premises use may be prepared as a spraying oil containing the active ingredient and the oil may soak the wick of a lamp which is then subjected to combustion. The concentration of the compound of formula I' in the oil is preferably 0.03 to 95% by weight.

The insecticidal compositions as well as the acaricidal and nematocidal compositions of the invention may also contain one or more other pesticides and are in the usual powder, granule, suspension, emulsion or solution form. For acaricide use, the compositions are preferably wettable powders for foliar spraying containing 1 to 80% of the active ingredient or liquids for foliar spraying containing 1 to 500 g/l of the active ingredient. Also useful are powders for foliar powdering containing 0.05 to 3% by weight of the active ingredient. For nematocide use, the compositions are in the form of liquids for soil treatment containing 300 to 500 g/l of the active ingredient. For acaricide and nematocide use, the preferred dose of the active compounds is 1 to 100 g per hectare.

To increase the biological activity of the compositions of the invention, classical synergists may be incorporated therein such as 1-(2,5,8-trioxadodecyl)-2-propyl-4,5-methylenedioxy-benzene (piperonyl butoxide) or N-(2-ethyl-heptyl)bicyclo-[2,2-1] 5-heptene-2,3-dicarboximide or piperonyl-bis-2-(2'-n-butoxy-ethoxy)-ethyl acetal (tropital).

When the compositions are to be used to combat parasitic acariens of animals, the active compounds of formula I' are very often incorporated into alimentary compositions in association with a nutritive mixture adapted to the animal to be fed. The nutritive mixture will vary depending upon the specific animal but usually contains cereals, sugars and grains, soybean press cake, peanuts and turnsole, meal of animal origin such as fish meal, synthetic amino acids, mineral salts, vitamins and antioxidants.

The compositions of the invention show an excellent general tolerance and are equally useful as medicaments for treating affections created by ticks and scabies. The compositions may be used in veterinary and human medicines. In human medicine, the compositions may be used to combat lice as well as prevent or treat scabies. The compositions may also be used as anthelmintics.

The said medicaments may be administered externally by vaporization, by shampoo, by painting or by bathing. For veterinary usage, the compositions may also be administered by painting the dorsal spine by the "pour on" method as well as being administered digestively or parenterally.

The compositions of the invention are also useful as biocides or to regulate growth.

Another feature of the invention are insecticidal, acaricidal or nematocidal compositions containing as an active ingredient at least one compound of formula I' and as a second active ingredient at least one pyrethrinoid ester selected from the group consisting of esters of allethrolone, of 3,4,5,6-tetrahydrophthalimidomethyl alcohol, of 5-benzyl-3-furylmethyl alcohol, of 3-phenoxy-benzyl alcohol and a α-cyano-3-phenoxy-benzyl alcohols with chrysanthemic acids, esters of 5-benzyl-3-furyl-methyl alcohol with 2,2-dimethyl-3-(2-oxo-3-tetrahydrothiophenylidene methyl)-cyclopropane-1-carboxylic acids, esters of 3-phenoxy-benzyl alcohol and α-cyano-3-phenoxy-benzyl alcohols with 2,2-dimethyl-3-(2,2-dichlorovinyl) cyclopropane-1-carboxylic acids, esters of α-cyano-3-phenoxybenzyl alcohols with 2,2-dimethyl-3-(2,2-dibromovinyl)-cyclopropane-1-carboxylic acids, esters of 3-phenoxy-benzyl alcohol with 2-p-chlorophenyl-2-isopropyl-acetic acids, esters of allethrolone, 3,4,5,6-tetrahydrophthalimidomethyl alcohol, 5-benzyl-3-furyl-methyl alcohol, 3-phenoxy-benzyl alcohol or α-cyano-3-phenoxy-benzyl alcohols with 2,2-dimethyl-3-(1,2,2,2-tetrahaloethyl)-cyclopropane-1-carboxylic acids where halo is fluorine, chlorine or bromine wherein the compounds of formula I' and the above pyrethrimoid esters are in all possible steroisomer forms.

The latter associated compositions of the invention are of particular interest for combatting by the polyvalence of their action, a large range of parasites or by manifesting a synergistic action in some cases.

The novel method of the invention for combatting parasites such as insects, nematodes and acariens comprises contacting the parasites with a pesticidally effective amount of at least one compound of formula I'.

In the following examples there are described several preferred embodiments to illustrate the invention. However, it should be understood that the invention is not intended to be limited to the specific embodiments.

EXAMPLE 1

(S)α-cyano-3-phenoxy-benzyl (1R,cis) 2,2-dimethyl-3-[(Z) 3-(2,2,2trifluoroethoxy)-3-oxo-1-propenyl]-cyclopropane-carboxylate

STEP A: 1,1-dimethylethyl (1R,cis) 2,2-dimethyl-3-(3-hydroxy-3-oxo-1-propynyl)-cyclopropane-carboxylate 26 g of 1,1-dimethylethyl (1R,cis) 2,2-dimethyl-3-(2,2-dibromovinyl)-cyclopropane-carboxylate were added to 175 ml of anhydrous tetrahydrofuran and 60 ml of a 20% solution of butyllithium in cyclohexane were then added thereto at −65° C. The mixture was stirred for 1 hour at −60° C. and then a current of carbon dioxide was bubbled through the mixture for an hour and a half. The reaction mixture was poured into iced water to which N sodium hydroxide had been added. The mixture was washed with ether and the alkaline aqueous phase was acidified to a pH of 4 and was extracted with ether. The organic phases were dried and evaporated to dryness under reduced pressure to obtain a product which was crystallized from petroleum ether (B. Pt. 60–80° C.) to obtain 8.3 g of 1,1-dimethylethyl (1R, cis) 2,2-dimethyl-3-(3-hydroxy-3-oxo-1-propynyl)-cyclopropane-carboxylate melting at 144° C.

NMR Spectrum (deuterochloroform):
Peaks at 1.22 and 1.37 ppm (hydrogens of geminal methyls); at 1.78 ppm (1- and 3-hydrogens of cyclopropane); at 1.47 ppm (hydrogens of tert.-butyl); at 8.25 ppm (hydrogen of

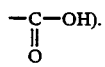

STEP B: 1,1-dimethylethyl (1R,cis) 2,2-dimethyl-3-[3-oxo-3-(2,2,2-trifluoroethoxy)-1-propynyl]-cyclopropane-carboxylate 4 g of the product of Step A and 3.5 g of dicyclohexylcarbodiimide were added to a solution of 20 ml of methylene chloride and 1 ml of pyridine and the reaction mixture was stirred for 1 hour. 2.15 g of trifluoroethanol and 5 ml of methylene chloride were then added to the mixture which was stirred at 20° C. for 16 hours and was filtered. The filtrate was rinsed with methylene chloride and the filtrate was evaporated to dryness. The residue was taken up in ether and the solution was washed with N hydrochloric acid, then with water and dried and evaporated to dryness. The 5 g of residue was chromatographed over silica gel and was eluted with a 95-5 benzene-ethyl acetate mixture to obtain 3.5 g of 1,1-dimethylethyl (1R,cis) 2,2-dimethyl-3-[3-oxo-3-(2,2,2-trifluoroethoxy)-1-propynyl]-cyclopropane-carboxylate.

NMR Spectrum (deuterochloroform):
Peaks at 1.2 and 1.37 ppm (hydrogens of geminal methyls); at 1.77 ppm (1- and 3-hydrogens of cyclopropane); at 1.43 ppm (hydrogens of the methyls of 1,1-dimethylethyl); at 4.3 to 4.7 ppm (hydrogen of trifluoroethoxy).

STEP C: (1R, cis) 2,2-dimethyl-3-[3-oxo-3-(2,2,2-trifluoroethoxy)-1-propynyl]-cyclopropane-carboxylic acid A mixture of 3.3 g of the compound of step B, 30 ml of toluene and 100 mg of p-toluene sulfonic acid was refluxed until gas evolution ceased and was then cooled, washed with water, dried and evaporated to dryness to obtain 2.6 g of (1R,cis) 2,2-dimethyl-3-[3-oxo-3-(2,2,2-trifluoroethoxy)-1-propynyl]-cyclopropane-carboxylic acid which was used as is in the following step.

STEP D: (1R,cis) 2,2-dimethyl-3-[(Z))-3-oxo-3-(2,2,2-trifluoroethoxy)-1-propenyl]-cyclopropane-carboxylic acid 500 mg of 10% palladium hydroxide on barium sulfate and 5 ml of ethyl acetate were placed in a round flask connected to a hydrogen apparatus and 2 g of the product of Step C, 45 ml of ethyl acetate and 0.5 ml of quinoline were added thereto. Hydrogenation was carried out until hydrogen absorption ceased and the mixture was filtered. The filtrate was washed with N hydrochloric acid, then with water and evaporated to dryness. The 2 g of residue were chromatographed over silica gel and eluted with a 70-20-1 cyclohexane-ethyl acetate-acetic acid mixture to obtain 1.3 g of (1R,cis) 2,2-dimethyl-3-[(Z )-3-oxo-3-(2,2,2-trifluoro-ethoxy)-1-propenyl]cyclopropane-carboxylic acid.

NMR Spectrum (deuterochloroform):
Peaks at 1.3 and 1.32 ppm (hydrogens of geminal methyls); at 1.92–2.06 ppm (1-hydrogen of cyclopropane); at 3.07 to 3.38 p (3-hydrogen of cyclopropane); at 6.6 to 6.9 ppm (1-hydrogen of propenyl); at 5.9–6.0 ppm (2-hydrogen of propenyl); at 4.3 to 4.7 ppm (hydrogen of trifluoroethoxy).

STEP E: (S)α-cyano-3-phenoxy-benzyl (1R,cis) 2,2dimethyl-3-[(Z) 3-(2,2,2-trifluoroethoxy)-3-oxo-1-propenyl]-cyclopropanecarboxylate 1.3 g of (1R,cis) 2,2-dimethyl-3-[(Z) 3-oxo-3-(2, 2,2-trifluoroethoxy)-1-propenyl]-cyclopropane-carboxylic acid, 0.1 ml of pyridine and 15 ml of methylene chloride were mixed with agitation and then 1.05 g of dicyclohexylcarbodiimide were added thereto. A solution of 1.35 g of (S)α-hydroxy-3-phenoxy-benzene-acetonitrile in 5 ml of methylene chloride were then added to the mixture which was stirred for 5 hours at ambient temperature and then was filtered. The filter was rinsed with methylene chloride and 2N hydrochloric acid was added to the filtrate. The decanted organic phase was washed with water, dried and evaporated to dryness. The oil residue was chromatographed over silica gel and was eluted with 95-5 cyclohexane-ethyl acetate mixture to obtain 1.33 g of (S)α-cyano-3-phenoxy-benzyl (1R,cis) 2,2-dimethyl-3-[(Z) 3-(2,2,2-trifluoroethoxy)-3-oxo-1-propenyl]-cyclopropane-carboxylate with a specific rotation of $[\alpha]_D^{20} = +42°\pm 2°$ (c=0.7% in benzene).

NMR Spectrum (deuterochloroform):
Peaks at 1.26 and 1.28 ppm (hydrogens of geminal methyls); at 1.97–2.11 ppm (1-hydrogen of cyclopropane); at 3.1 to 3.4 ppm (3-hydrogen of cyclopropane); at 6.5 to 6.9 ppm (1-hydrogen of propenyl); at 5.9–5.93 ppm (2-hydrogen of propenyl); at 6.3 ppm (hydrogen on carbon attached to —CN); at 4.3 to 4.7 ppm (hydrogen of trifluoroethoxy).

EXAMPLE 2

(1S) 2,2-dimethyl-4-oxo-3-(2-propenyl)-2-cyclopenten-1-yl (1R,cis) 2,2-dimethyl-3-[(Z) 3-oxo-3-(2,2,2-trifluoroethoxy)-1-propenyl]-cyclopropane-carboxylate A mixture of 1.9 g of (1R,cis) 2,2-dimethyl-3-[(Z) 3-oxo-3-(2,2,2-trifluoroethoxy)-1-propenyl]-cyclopropane-carboxylic acid, 12 ml of methylene chloride and 100 mg of 4-dimethylamino-pyrimidine was admixed with 1.4 g of dicyclohexylcarbodiimide and then 1.1 g of (S) 3-(2-propenyl)-1-hydroxy-2-methyl-4-oxo-cyclopent-2-ene and 5 ml of methylene chloride were added thereto. The mixture was stirred at room temperature for 2 hours and was then filtered. The filtrate was washed with 0.5N hydrochloric acid, then with water, dried and evaporated to dryness. The 3 g of residue were chromatographed over silica gel and eluted with a 95-5 benzene-ethyl acetate mixture to obtain 2.2 g of (1S) 2,2-dimethyl-4-oxo-3-(2-propenyl)-2-cyclopenten-1-yl (1R,cis) 2,2-dimethyl-3-[(Z) 3-oxo-3-(2,2,2-trifluoroethoxy)-1-propenyl]-cyclopropane-carboxylate with a specific rotation of $[\alpha]_D^{20} = +38° \pm 2.5°$ (c=0.5% in benzene).

NMR Spectrum (deuterochloroform):
Peaks at 1.29 and 1.32 ppm (hydrogens of geminal methyls); at 1.97–2.11 ppm (1-hydrogen of cyclopropane); at 3.05 to 3.37 ppm (3-hydrogen of cyclopropane); at 6.7 to 7 ppm (1-hydrogen of propenyl); at 5.9–6.1 ppm (2-hydrogen of propenyl); at 4.3 to 4.75 ppm (hydrogen of trifluoroethoxy); at 5.7 ppm (hydrogen of cyclopentene α to CO); at 2 ppm (hydrogen of methyl on cyclopentene); at 4.8 to 5.25 ppm (3-hydrogen of propenyl).

EXAMPLE 3

(1S)α-cyano-3-phenoxy-benzyl (1R,cis) 2,2-dimethyl-3-[(Z) 3-oxo-3-benzyloxy-1-propenyl]-cyclopropane-carboxylate STEP A: 1,1-dimethylethyl (1R,cis) 2,2-dimethyl-3-[(Z) 2-carboxy ethenyl]-cyclopropane-carboxylate 2 g of 1,1-dimethylethyl (1R,cis) 2,2-dimethyl-3[2-carboxyethynyl]-cyclopropane-carboxylate in 41 ml of ethyl acetate were hydrogenated in the presence of 0.38 g of 10% palladium hydroxide on barium sulfate and 0.4 ml of quinoline and the mixture was filtered. The filtrate was washed with 0.5N hydrochloric acid, then with water until neutral, dried and evaporated to dryness under reduced pressure to obtain 2 g of 1,1-dimethylethyl (1R,cis) 2,2-dimethyl-3-[(Z) 2-carboxyethenyl]-cyclopropane-carboxylate melting at 94° C.

STEP B: 1,1-dimethylethyl (1R,cis) 2,2-dimethyl-3-[(Z)-3-oxo-3-benzyloxy-1-propenyl]-cyclopropane-carboxylate 2.4 g of the product of Step A were added to 20 ml of ethyl acetate and 2.34 g of O-benzyl-N,N-diisopropyl-isoure (described by ESCHIMDT et al, Liebig Ann. Chem. Vol. 685 (1965 p. 161) were then added thereto. The mixture was stirred for 16 hours at room temperature and was filtered. The filtrate was evaporated to dryness under reduced pressure and the 4.3 g of yellow oil were chromatographed over silica gel and eluted with a 7-3 benzene-cyclohexane mixture to obtain 2 g of 1,1-dimethylethyl (1R,cis) 2,2-dimethyl-3-[(Z)-3-oxo-3-benzyloxy-1-propenyl]-cyclopropane-carboxylate.

NMR Spectrum (deuterochloroform):
Peaks at 1.22 and 1.28 ppm (hydrogens of geminal methyls); at 1.77–1.91 ppm (1-hydrogen of cyclopropane); at 2.98 to 3.3 ppm (3-hydrogen of cyclopropane); at 6.5 to 6.8 ppm (1-hydrogen of propenyl); at 5.8–6 ppm (2-hydrogen of propenyl); at 1.43 ppm (hydrogens of the methyls of dimethylethyl); at 5.1 ppm (hydrogens of methoxy of benzyloxy).

STEP C: (1R,cis) 2,2-dimethyl-3-[(Z)-3-oxo-3-benzyloxy-1-propenyl]-cyclopropane-carboxylic acid A mixture of 2 g of the product of Step B, 30 ml of toluene and 100 mg of p-toluene sulfonic acid was stirred at 90° C. for 2 hours and was then evaporated to dryness. The 2 g of residue were chromatographed over silica gel and eluted with a 60-40-1 cyclohexane-ethyl acetate-acetic acid mixture to obtain 1.4 g of (1R,cis) 2,2-dimethyl-3-[(Z) 3-oxo-3-benzyloxy-1-propenyl]-cyclopropane-carboxylic acid.

NMR Spectrum (deuterochloroform):
Peaks at 1.25 and 1.3 ppm (hydrogens of geminal methyls); at 1.84–1.98 ppm (1-hydrogen of cyclopropane); at 3.14 to 3.43 ppm (3-hydrogen of cyclopropane); at 6.4 to 6.77 ppm (1-hydrogen of propenyl); at 5.98 ppm (2-hydrogen of propenyl).

STEP D: (1R,cis) 2,2-dimethyl-3-[(Z) 3-oxo-3-benzyloxy-1-propenyl]-cyclopropane-carboxylic acid chloride A mixture of 1.6 g of (1R,cis) 2,2-dimethyl-3[(Z) 3-oxo-3-benzyloxy-1-propenyl]-cyclopropane carboxylic acid, 10 ml of isoprene and 1 ml of thionyl chloride was stirred for 5 hours under a current of nitrogen and then was concentrated to obtain 2 g of (1R,cis) 2,2-dimethyl-3[(Z) 3-oxo-3-benzyloxy-1-propenyl]-cyclopropane-carboxylic acid chloride which was concentrated to obtain 2 g of (1R,cis) 2,2-dimethyl-3-[(Z) 3-oxo-3-benzyloxy-1-propenyl]-cycloropane-carboxylic acid chloride which was used as in the following step.

STEP E: (1S)α-cyano-3-phenoxy-benzyl (1R,cis) 2,2-dimethyl-3-[(Z) 3-oxo-3-benzyloxy-1-propenyl]-cyclopropane-carboxylate 1 g of the product of Step D was added to a solution of 700 mg of (S)α-hydroxy-3-phenoxy-benzene-acetonitrile, 20 ml of benzene and 0.6 ml of pyridine and the reaction mixture was stirred for 16 hours at room temperature and was then in to a mixture of iced water and N hydrochloric acid. The suspension was stirred and extracted with benzene and the benzene extracts were washed with water, dried, filtered and evaported to dryness. The 1.5 g of residue were chromatographed over silica gel and eluted with an 8-2 cyclohexane-ethyl acetate mixture to obtain 861 mg of (1S)α-cyano-3-phenoxy-benzyl (1R,cis) 2,2-dimethyl-3-[(Z) 3-oxo-3-benzyloxy-1-propenyl]-cyclopropane-carboxylate melting at 83° C. and having a specific rotation of $[\alpha]_D^{20} = +69° \pm 5°$ (c=0.2% in benzene).

NMR Spectrum (deuterochloroform):
Peaks at 1.25 ppm (hydrogens of geminal methyls); at 6.33 ppm (hydrogen on carbon attached to —CN).

EXAMPLE 4

(1S)-2-methyl-4-oxo-3-(2-propenyl)-2-cyclopenten-1-yl (1R, cis) 2,2-dimethyl-3-[(Z) 3-oxo-3-benzyloxy-1-propenyl]-cyclopropane-carboxylate 1 g of (1R,cis) 2,2-dimethyl-3-[(Z) 3-oxo-3-benzyloxy-1-propenyl]-cyclopropane-carboxylic acid chloride was added to a mixture of 450 mg of (S) 3-(2-propenyl)-1-hydroxy-2-methyl-4-oxo-cyclopent-2-en-1-yl, 20 ml of benzene and 0.6 ml of pyridine and the mixture was stirred for 6 hours and was then poured into a mixture of iced water and N hydrochloric acid. The mixture was extracted with benzene and the combined benzene phases was washed with water, dried and evaporated to dryness. The 1.5 g of residue was chromatographed over silica gel and was eluted with an 8-2 cyclohexane-ethyl acetate mixture to obtain (1S) 2-methyl-4-oxo-3-(2propenyl)-2-cyclopenten-1-yl (1R,cis) 2,2-dimethyl-3-[(Z) 3-oxo-3-benzyloxy-1-propenyl]-cyclopropane-carboxylate having a specific rotation of $[\alpha]_D^{20} = +37° \pm 2.5$ (c=0.5% in benzene).

NMR Spectrum (deuterochloroform):

Peaks at 1.27 and 1.31 ppm (hydrogens of geminal methyls); at 1.87–2 ppm (1-hydrogen of cyclopropane); at 3.12 to 2.45 ppm (3-hydrogen of cyclopropane); at 5.8 to 6.8 ppm (1-and 2-hydrogens of propenyl); at 5.2 ppm (hydrogens of methoxy of benzyloxy); at 5.6 to 5.7 ppm (hydrogen of cyclopentene α to $CO_2$); at 2 ppm (hydrogens of methyl on the cyclopropane); at 4.8 to 5.2 ppm (hydrogens of propenyl on the cyclopropane).

EXAMPLE 5

(S)α-cyano-3-phenoxy-benzyl (1R,cis) 2,2-dimethyl-3-[(Z) 3-oxo-3-phenoxy-1-propenyl]-cyclopropane-carboxylate

STEP A: 1,1-dimethylethyl (1R,cis) 2,2-dimethyl-3-[3-oxo-3-phenoxy-1-propynyl]-cyclopropane-carboxylate A solution of 25 g of 1,1-dimethylethyl (1R,cis) 2,2-dimethyl-3-(2', 2'-dibromovinyl)-cyclopropane-carboxylate in 250 ml of tetrahydrofuran was admixed with 48 ml of a 20% solution of butyllithium in cyclohexane with stirring at −65° C. and the mixture was stirred for one hour at −65° C. 9.6 ml of phenyl chloroformate were added to mixture which was then stirred at −65° C. for one hour. The temperature was allowed to return to room temperature while the stirring was maintained and the mixture was poured into a saturated aqueous solution of monosodium phosphate. The mixture was extracted with ether and the ether phase was washed with water and dried. The 24.6 g of oil residue was chromatographed over silica gel and was eluted with a 9-1 cyclohexane-ethyl acetate mixture to obtain 14.4 g of 1,1-dimethylethyl (1R,cis) 2,2-dimethyl-3-[3-oxo-3-phenoxy-1-propynyl]-cyclopropane-carboxylate.

NMR Spectrum (deuterochloroform):

Peaks at 1.23 and 1.42 ppm (hydrogens of geminal methyls); at 1.82 ppm (1- and 3-hydrogens of cyclopropane); at 1.5 ppm (hydrogens of dimethylethyl); at 7 to 7.6 ppm (aromatic hydrogens).

STEP B: 1,1-dimethylethyl (1R,cis) 2,2-dimethyl-3-[(Z) 3-oxo-3-phenoxy-1-propenyl]-cyclopropane-carboxylate In the presence of 800 mg of palladium hydroxide on barium sulfate, 0.8 ml of quinoline and 20 ml of ethyl acetate, 4 g of the product of Step A in solution in 60 ml of ethyl acetate were hydrogenated and the mixture was filtered 200 ml of a 2N solution of hydrochloric acid were added to the filtrate and the decanted organic phase was washed with water and dried. The 4.1 g of an oil residue were chromatographed over silic gel and eluted with a 95-5 cyclohexane-ethyl acetate mixture to obtain 3.35 g of 1,1-dimethylethyl (1R,cis) 2,2-dimethyl-3-[(Z) 3-oxo-3-phenoxy-1-propenyl]-cyclopropane-carboxylate.

NMR Spectrum (deuterochloroform):

Peaks at 1.23 and 1.3 ppm (hydrogens of geminal methyls); at 1.83–1.97 ppm (1-hydrogen of cyclopropane); at 3 to 3.33 ppm (3-hydrogen of cyclopropane); 1.44 ppm (hydrogens of methylethyl); at 6.7 to 7 ppm (1-hydrogen of propenyl); at 6.03–6.21 ppm (2-hydrogen of propenyl); at 7 to 7.5 ppm (aromatic hydrogens).

STEP C: (1R,cis) 2,2-dimethyl-3-[(Z) 3-oxo-3-phenoxy-1-propenyl]-cyclopropane-carboxylic acid A mixture of 3.3 g of the product of Step B, 35 ml of toluene and 100 mg of monohydrated p-toluene sulfonic acid was refluxed until gas evolution ceased and then was evaporated to dryness under reduced pressure. The 3.4 g residue were chromatographed over silica gel and eluted with a 70-30-1 cyclohexane-ethyl acetate acetic acid mixture to obtain 2.4 g of (1R,cis) 2,2-dimethyl-3-[(Z) 3-oxo-3-phenoxyl-propenyl]-cyclopropane-carboxylic acid melting at 57° C.

NMR Spectrum (deuterochloroform):

Peaks at 1.25 to 1.33 ppm (hydrogens of geminal methyls); at 1.9–2.04 ppm (1-hydrogen of cyclopropane); at 3.2 to 3.5 ppm (3-hydrogen of cyclopropane); at 6.6 to 6.9 ppm (1-hydrogen of propenyl); at 6.0–6.2 ppm (2-hydrogen of propenyl).

STEP D: (S)α-cyano-3-phenoxy-benzyl (1R,cis) 2,2-dimethyl-3-[(Z) 3-oxo-3-phenoxy-1-propenyl]-cyclopropane-carboxylate Using the procedure of Example 1, 1.5 g of (1R,cis) 2,2-dimethyl-3-[(Z) 3-oxo-3-phenoxy-1-propenyl]-cyclopropane-carboxylic acid and 1.45 g of (S)α-cyano-3-phenoxy-benzyl-acetonitrile were reacted to obtain 1.8 g of (S)α-cyano-3-phenoxybenzyl (1R,cis) 2,2-dimethyl-3-[(Z) 3-oxo-3-phenoxy-1-propenyl]cyclopropane-carboxylate with a specific rotation of $[\alpha]_D^{20} = +54° \pm 2.5°$ (c=0.5% in benzene).

NMR Spectrum (deuterochloroform):

Peaks at 1.25 ppm (hydrogens of geminal methyls); at 1.97–2.12 ppm (1-hydrogen of cyclopropane); at 3.25 to 3.6 ppm (3-hydrogen of cyclopropane); at 6.6 to 7 ppm (1-hydrogen of propenyl) at 6.1–6.3 ppm (2-hydrogen of propenyl); at 6.9 to 7.7 ppm (aromatic hydrogens of 3-phenoxy-phenyl).

EXAMPLE 6

(1S) 2-methyl-4-oxo-3-(2-propenyl)-2-cyclopenten-1-yl (1R,cis) 2,2-dimethyl-3-[(Z) 3-oxo-3-phenoxy-1-propenyl]-cyclopropane-carboxylate Using the procedure of Example 2, 1.5 g of (1R,cis) 2,2-dimethyl-3-[(Z) 3-oxo-3-phenoxy-1-propenyl]-cyclopropane-carboxylic acid and 1 g of (S) 3-(2-propenyl)-1-hydroxy-2-methyl-4-oxo-cyclopent-2-en-1-yl were reacted to obtain 1.6 g of (1S) 2-methyl-4-oxo-3-(2-propenyl)-2-cyclopenten-1-yl (1R, cis) 2,2-dimethyl-3-[(Z) 3-oxo-3-phenoxy-1-propenyl]-cyclopropane-carboxylate with a specific rotation of $[\alpha]_D^{20} = +66° \pm 2.5$ (c=0.5% in benzene).

NMR Spectrum (deuterochloroform):

Peaks at 1.26 and 1.33 ppm (hydrogens of geminal methyls); at 1.95–2.09 ppm (1-hydrogen of cyclopropane); at 5.7 ppm (hydrogen of cyclopentene $\alpha$ $CO_2$); at 4.8 to 5.2 ppm (3-hydrogen of propenyl on the cyclopentene); at 2 ppm (hydrogens of methyl on the cyclopentene); at 6.1 to 6.7 ppm (hydrogens of propenyl on the cyclopropane); at 7 to 7.7 ppm (aromatic hydrogens).

EXAMPLE 7

(RS)$\alpha$-cyano-3-phenoxy-benzyl (1R,cis) 2,2-dimethyl-3-[(Z) 3-oxo-3-methoxymethoxy-1-propenyl]-cyclopropane-carboxylate STEP A: (RS)$\alpha$-cyano-3-phenoxy-benzyl (1R,cis) 2,2-dimethyl-3-(3-oxo-3-methoxymethoxy-1-propynyl)-cyclopropane-carboxylate A solution of 3 g of (RS)$\alpha$-cyano-3-phenoxy-benzyl (1R,cis) 2,2-dimethyl-3-(3-hydroxy-3-oxo-1-propynyl)-cyclopropane-carboxylate in 30 ml of anhydrous dimethylformamide was cooled to +10° C. and 300 mg of 61% sodium hydride in oil were added in portions thereto. Then, over 15 minutes, 2.5 ml of chloromethyl ether solution prepared by mixing 4.5 ml of methylal and 0.52 ml of methanol and slowly adding 3.53 ml of acetyl chloride after which the mixture was stirred for 36 hours at room temperature. The mixture was stirred for 2 hours and was then poured into an aqueous solution of monosodium phosphate. The mixture was extracted with ethyl acetate and the organic phase was washed with water, dried and evaporated to dryness. The residue was chromatographed over silica gel and eluted with a 75-25 mixture of cyclohexane-ethyl acetate to obtain 2 g of (RS) $\alpha$-cyano-3-phenoxy-benzyl (1R,cis) 2,2-dimethyl-3-(3-oxo-3-methoxymethyl-1-propynyl)-cyclopropane-carboxylate.

NMR Spectrum (deuterochloroform):

Peaks at 1.23–1.27 ppm and 1.35–1.45 ppm (hydrogens of geminal methyls); at 1.95 ppm (1- and 3-hydrogens of cyclopropane); at 5.28 ppm (hydrogens of methylene of methoxymethoxy); at 3.5 ppm (hydrogens of methyl of methoxymethoxy); at 6.42 and 6.47 ppm (hydrogen on carbon attached to —CN); at 6.92 to 7.58 ppm (aromatic hydrogens).

STEP B (RS) $\alpha$-cyano-3-phenoxy-benzyl (1R,cis) 2,2-dimethyl-3-[(Z) 3-oxo-3-methoxymethoxy-1-propenyl]-cyclopropane-carboxylate 2.2 g of the product of Step A in 50 ml of ethyl acetate were hydrogenated in the presence of 450 mg of 10% palladium hydroxide on barium sulfate in 30 ml of ethyl acetate and 0.5 ml of quinoline and the mixture was filtered. The filtrate was washed with N hydrochloric acid and with water, dried and evaporated to dryness. The residue was chromatographed over silica gel and eluted with a 8-2 mixture of cyclohexane-ethyl acetate to obtain 1.2 g of (RS)$\alpha$-cyano-3-phenoxy-benzyl (1R,cis) 2,2-dimethyl-3-[(Z) 3-oxo-3-methoxymethoxy-1-propenyl]-cyclopropane-carboxylate with a specific rotation of $[\alpha]_D^{20} = +41° \pm 3$ (c=0.3% in $CHCl_3$).

NMR Spectrum (deuterochloroform):

Peaks at 1.27–1.28 ppm and 1.33–1.35 ppm (hydrogens of geminal methyls); at 1.93–2.1 ppm (1-hydrogen of cyclopropane); at 3.17 to 3.5 ppm (3-hydrogen of cyclopropane); 6.47 to 6.82 ppm (ethylenic 1-hydrogen); at 5.85–6.0 ppm and 5.88–6.1 ppm (ethylenic 2-hydrogen); at 5.27 and 5.3 ppm (hydrogens of $CH_2O$ methoxy); at 3.47 and 3.5 ppm (hydrogens of methyl methoxy) at 6.4 ppm (hydrogen on carbon attached to —CN); at 6.92 to 7.67 ppm (aromatic hydrogens).

The (RS)$\alpha$-cyano-3-phenoxy-benzyl (1R,cis) 2,2-dimethyl-3-[3-hydroxy-3-oxo-1-propynyl]-cyclopropane-carboxylate used as the starting material of Step A can be prepared in a manner similar to that for the (S) ester described infra using the corresponding (RS) alcohol.

EXAMPLE 8

(S)$\alpha$-cyano-3-phenoxy-benzyl (1R,cis) 2,2-dimethyl-3-[(Z) 3-oxo-3l-cyano-methoxy-1-propenyl]-cyclopropane-carboxylate Step A: (RS)$\alpha$-cyano-3-phenoxy-benzyl (1R,cis) 2,2-dimethyl-3-[3-oxo-3-cyano-methoxy-1-propynyl]-cyclopropane-carboxylate Using the procedure of Example 7, 2 ml of chloroacetonitrile were reacted and after extraction with ether and elution with a 9-1 mixture of cyclohexane-ethyl acetate, 2.69 g of (RS)$\alpha$-cyano-3-phenoxy-benzyl (1R,cis) 2,2-dimethyl-3-[3-oxo-3-cyano-methoxy-1-propynyl]-cyclopropane-carboxylate were obtained.

STEP B: (RS)$\alpha$-cyano-3-phenoxy-benzyl (1R,cis) 2,2-dimethyl-3-[(Z) 3-oxo-3-cyanomethoxy-1-propenyl]-cyclopropane-carboxylate Using the procedure of Example 7, 2.69 g of the product of Step A were reacted to obtain 2.02 g of (RS)$\alpha$-cyano-3-phenoxy-benzyl (1R,cis) 2,2-dimethyl-3-[(Z) 3-oxo-3-cyanomethoxy-1-propenyl]-cyclopropane-carboxylate after elution with a 9-1 mixture of cyclohexane-ethyl acetate.

STEP C: (S)$\alpha$-cyano-3-phenoxy-benzyl (1R,cis) 2,2-dimethyl-3-[(Z) 3-oxo-3-cyanomethoxy-1-propenyl]-cyclopropane-carboxylate 1.4 g of the product of Step B were chromatographed over silica gel and eluted with methylene chloride to obtain 0.41 g of (S)$\alpha$-cyano-3-phenoxy-benzyl (1R,cis) 2,2-dimethyl-3 [(Z) 3-oxo-3-cyanomethoxy-1-propenyl]-cyclopropane-carboxylate with a specific rotation of
$[\alpha_D^{20} = +55° \pm 1.5$ (c=1% in $CHCl_3$).

EXAMPLE 9

(S)α-cyano-3-phenoxy-benzyl (1R,cis) 2,2-dimethyl-3-[(Z) 3-oxo-3-ethoxyethoxy-1-propenyl]-cyclopropane-carboxylate STEP A: Tert.-butyl (1R,cis) 2,2-dimethyl-3-[2-carboxyethynyl]-cyclopropane-carboxylate A mixture of 26 g of tert.-butyl (1R,cis) 2,2-dimethyl-3-(2,2-dibromovinyl)-cyclopropane-carboxylate in 175 ml of anhydrous tetrahydrofuran was admixed with 60 ml of a 20% solution of butyllithium in cyclohexane at −65° C. and mixture was stirred for 1 hour at −60° C. The, a current of carbon dioxide was bubbled in for an hour and a half and the reaction mixture was poured into ice water to which had been added N sodium hydroxide. The mixture was washed with ether and the alkaline aqueous phase was acidified to a pH of 4 and was extracted with ether. The organic phases were dried and evaporated to dryness under reduced pressure and the residue was crystallized from petroleum ether (B.Pt. 60 −80° C.) to obtain 8.3 g of tert. -butyl (1R,cis) 2,2-dimethyl-3-[2-carboxyethynyl]-cyclopropane-carboxylate melting at 144° C.

NMR Spectrum (deuterochloroform):

Peaks at 1.22 and 1.37 ppm (hydrogens of geminal methyls); at 1.78 ppm (1- and 3-hydrogens of cyclopropane); at 1.47 ppm (hydrogens of tert.-butyl); at 8.25 ppm (hydrogen of

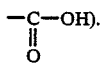

STEP B: Tert.-butyl (1R,cis) 2,2-dimethyl-3-(2,2,2-trichloroethoxycarbonylethynyl)-cyclopropane-carboxylate 6.2 g of dicyclohexylcarbodiimide were introduced into a solution of 7.15 g of tert.-butyl (1R,cis) 2,2-dimethyl-3-(2-carboxyethynyl)-cyclopropane-carboxylate and 80 mg of 4-dimethylamino-pyridine in 35 ml of methylene chloride and the reaction mixture was stirred for 10 minutes after which 4.5 of 2,2,2-trichloroethanol were added. The mixture was stirred for 1 hour and was filtered. The filtrate was washed with N hydrochloric acid, then with water until neutral, dried and evaporated to dryness. The 14 g of oil residue were chromatographed over silica gel and eluted with a 97-3 mixture of benzene-ethyl acetate to obtain 9 g of tert.butyl (1R,cis) 2,2-dimethyl-3-(2,2,2-trichloroethoxycarbonylethynyl)-cyclopropane-carboxylate melting at 70–71° C.

STEP C: (1R,cis) 2,2-dimethyl-3-(2,2,2-trichloroethoxycarbonylethynyl)-cyclopropane-carboxylic acid A mixture of 11.4 g of the product of Step B, 120 ml of toluene and 300 mg of p-toluene sulfonic acid was refluxed for 1 hour and was allowed to return to room temperature. The reaction mixture was washed with water, dried and evaporated to dryness to obtain 9.5 of (1R,cis) 2,2-dimethy-3-(2,2,2-trichloroethoxycarbonylethynyl)-cyclopropane-carboxylic acid which was used as is for the following step.

STEP D: (S)α-cyano-3-phenoxy-benzyl (1R,cis) 2,2-dimethyl-3-(2,2,2-trichloroethoxycarbonylethynyl)-cyclopropane-carboxylate 6.2 g of dicyclohexycarbodiimide were added to a solution of 9.5 g of the product of Step C, 30 ml of methylene chloride and 3 ml of pyridine and the reaction mixture was stirred for half and hour. 6.8 g of (S)α-cyano-3-phenoxy-benzyl alcohol were added thereto and the mixture was stirred for an hour and half and filtered. The filtrate was washed with N hydrochloric acid, then with water until neutral, dried, and evaporated to dryness. The 15.3 g of oil residue were chromatographed over silica gel and eluted with a 97-3 mixture of benzene-ethyl acetate to obtain 12 g of (S)α-cyano-3-phenoxy-benzyl (1R,cis) 2,2-dimethyl-3-(2,2,2-trichloroethoxycarbonylethynyl)-cyclopropane-carboxylate melting at 101° C.

STEP E: (S)α-cyano-3-phenoxy-benzyl (1R,cis) 2,2-dimethyl-3-(3-hydroxy-3-oxo-propynyl)-cyclopropane-carboxylate 5.9 g of zinc powder were introduced into a solution of 6.5 g of the product of Step D, 23.4 ml of acetic acid and 2.6 ml of water and the mixture was stirred for 1 hour and filtered. The filtrate was decanted and the organic phase was washed with water. The aqueous phase was extracted with methylene chloride and the combined organic phases were dried, filtered and evaporated to dryness to obtain 4.7 g of (S) α-cyano-3-phenoxy-benzyl (1R,cis) 2,2-dimethyl-3-(3-hydroxy-3-oxo-propynyl)-cyclopropane-carboxylate which was used as is for the next step.

STEP F: (S)α-cyano-3-phenoxy-benzyl (1R,cis) 2,2-dimethyl-3-[3-oxo-3-ethoxyethoxy-1-propynyl]-cyclopropane-carboxylate A mixture of 2 g of (S)α-cyano-3-phenoxy-benzyl (1R,cis) 2,2-dimethyl-3-[3-hydroxy-3-oxo-1-propynyl]-cyclopropane-carboxylate, 20 ml of methylene chloride and 0.7 ml of ethoxyethanol cooled to 0 to +5° C. was admixed with a mixture of 1.1 g of dicyclohexylcarbodiimide, 5 ml of methylene chloride and 15 mg of 4-dimethylamino-pyridine and the mixture was stirred for 1 hour at +5° C. and for 2 hours at room temperature and was filtered. The filtrate was evaporated to dryness and the residue was chromatographed over silica gel and eluted with a 3-1 mixture of cyclohexane-ethyl acetate to obtain 1.3 g of (S)α-cyano-3-phenoxy-benzyl (1R,cis) 2,2-dimethyl-3-[3-oxo-3-ethoxyethoxy-1-propynyl]-cyclopropane-carboxylate.

NMR Spectrum (deuterochloroform):

Peaks at 1.22–1.32 ppm (hydrogens of geminal methyls); at 1.93 ppm (1- and 3-hydrogen of cyclopropane); at 4.17 to 4.3 ppm (1-hydrogens of COO—CH$_2$—CH$_2$—O); at 3.55 to 3.73 ppm (2-hydrogens of $\overline{COO}$—CH$_2$—CH$_2$—O); at 6.57 ppm (hydrogen on carbon attached to —CN); at 7 to 7.67 ppm (aromatic hydrogens); at 1.08–1.2–1.3 and 1.52 ppm (q) (hydrogens of ethyl).

STEP G: (S)α-cyano-3-phenoxy-benzyl (1R,cis) 2,2-dimethyl-3-[(Z) 3-oxo-3-ethoxyethoxy-1-propenyl]-cyclopropane-carboxylate Using the procedure of Step B of Example 7, 1.3 g of the products of Step F were reacted to obtain 1.0 g of (S)α-cyano-3-phenoxy-benzyl (1R,cis) 2,2-dimethyl-3-[(Z) 3-oxo-3-ethoxyethoxy-1-propenyl]-cyclopropanecarboxylate with a specific rotation of $[\alpha]_D^{20} = +37.5° \pm 2.5$ (c=0.5% in CHCl$_3$).

EXAMPLE 10

(S)α-cyano-3-phenoxy-benzyl (1R,cis) 2,2-dimethyl-3-[(Z) 3-oxo-3-(RS) (1,1,1-trifluoromethyl-ethoxy)-1-propenyl]-cyclopropane-carboxylate

STEP A: (S) α-cyano-3-phenoxy-benzyl (1R,cis) 2,2-dimethyl-3-[3-oxo-3-(RS)-1,1,1-trifluoromethylethoxy)-propynyl]-cyclopropane-carboxylate Using the procedure of Step F of Example 9, 4.6 g of 1,1,1-trifluoromethyl-ethanol and 3.8 g of (S)α-cyano-3-phenoxy-benzyl (1R,cis) 2,2-dimethyl-3-[3-oxo-3-hydroxypropynyl]-cyclopropane-carboxylate were reacted to obtain after elution with a 8-2 mixture of cyclohexane-ethyl acetate 2.6 of (S)α-cyano-3-phenoxybenzyl (1R,cis) 2,2-dimethyl-3-[3-oxo-3-(RS)-1,1,1-trifluoromethylethoxy)-propynyl]-cyclopropane-carboxylate.

STEP B: (S)α-cyano-3-phenoxy-benzyl (1R,cis) 2,2-dimethyl-3-[(Z) 3-oxo-3-(RS) (1,1,1-trifluoromethylethoxy)-1-propenyl]-cyclopropane-carboxylate Using the procedure of Step B of Example 7, 2.6 g of (S)α-cyano-3-phenoxy-benzyl (1R,cis) 2,2-dimethyl-3-[3-oxo-3-(RS)-1,1,1-trifluoromethylethoxy)-1-propynyl]-cyclopropane-1-carboxylate were reacted to obtain after elution with a 9-1-cyclohexane-ethyl acetate mixture 2.1 g of (S)α-cyano-3-phenoxy-benzyl (1R,cis) 2,2-dimethyl-3-[(Z) 3-oxo-3-(RS) (1,1,1-trifluoromethylethoxy)-1-propenyl]-cyclopropane-carboxylate with a specific rotation of $[\alpha]_D^{20} = +44° \pm 2°$ (c=0.4% in benzene).

EXAMPLE 11

(S)α-cyano-3-phenoxy-benzyl (1R,cis) 2,2-dimethyl-3-[(Z) 3-oxo-3-(2,2-difluoroethoxy)-1-propenyl]-cyclopropane-carboxylate

STEP A: Tert.-butyl (1R,cis) 2,2-dimethyl 3-[(Z) 3-hydroxy-3-oxo-1-propenyl]-cyclopropane-carboxylate A mixture of 2 g of tert.-butyl (1R,cis) 2,2-dimethyl-3-[2-carboxyethynyl]-cyclopropane-carboxylate in 40 ml of ethyl acetate was hydrogenated in the presence of 0.38 g of 10% palladium hydroxide on barium sulfate and 0.4 ml of quinoline and was filtered. The filtrate was washed with 0.5N hydrochloric acid, then with water until neutral, dried and evaporated to dryness under reduced pressure to obtain 2 of tert.-butyl (1R,cis) 2,2-dimethyl 3-[(Z) 3-hydroxy-3-oxo-propenyl]-cyclopropane-carboxylate melting at 94° C.

STEP B: Tert.butyl (1R,cis) 2,2-dimethyl-3-[3-oxo-3-(2,2-difluoroethoxy)-1-propynyl]-cyclopropane-carboxylate Using the procedure of Step F of Example 9, 5 g of tert.-butyl (1R,cis) 2,2-dimethyl-3-[3-hydroxy-3-oxo-1-propynyl]-cyclopropane-carboxylate were reacted to obtain after elution with a 7-3 mixture of n-hexane-isopropyl ether 5.25 g of tert.-butyl (1R,cis) 2,2-dimethyl-3-[3-oxo-3-(2,2-difluoroethoxy)-1-propynyl]-cyclopropane-carboxylate.

IR Spectrum (CHCl$_3$):

Absorption at 2232 cm$^{-1}$ (conjugated C≡C); at 1725 cm$^{-1}$ (ester carbonyl); at 1710 cm$^{-1}$ (asymetric); at 1393 cm$^{-1}$ and 1380 (gem. dimethyls); at 1372 cm$^{-1}$ (tert.-butyl).

STEP C: (1R,cis) 2,2-dimethyl-3-[3-oxo-3-(2,2-difluoroethoxy-1-propynyl]-cyclopropane-carboxylic acid A mixture of 5.2 g of the product of Step B and 500 g of p-toluene sulfonic acid in 40 ml of toluene was refluxed for 25 minutes and after cooling, 400 ml of ether were added thereto. The mixture was washed with water and the organic phase was dried and evaporated to dryness to obtain 4.1 g of (1R,cis) 2,2-dimethyl-3-[3-oxo-3-(2,2-difluoroethoxy)-1-propynyl]-cyclopropane-carboxylic acid.

STEP D: (S)α-cyano-3-phenoxy-benzyl (1R,cis) 2,2-dimethyl-3-]3-oxo-3-(2,2-difluoroethoxy)-1-propynyl]-cyclopropane-carboxylate Using the procedure of Step F of Example 9, 4.1 of the acid of Step C and 4.5 g of (S)α-cyano-3-phenoxybenzyl alcohol were reacted to obtain 4.7 g of (S)α-cyano-3-phenoxy-benzyl (1R,cis) 2,2-dimethyl-3-[3-oxo-3-(2,2-difluoroethoxy-1-propynyl]-cyclopropane-carboxylate after elution with a 6-4 mixture of petroleum ether (B. Pt. 40–70° C.)-isopropyl ether.

IR SPECTRUM (CHCl$_3$):

Absorption at 3580 cm$^{-1}$ (OH); at 1392 cm$^{-1}$ and 1380 cm$^{-1}$ (gem. dimethy at 2235 cm$^{-1}$ (conjugated C≡C); at 1755 cm$^{-1}$ (ester carbonyl); at 1725 (conjugated ester); at 1588 cm$^{-1}$ and 1488 cm$^{-1}$ (aromatics).

STEP E: (S)α-cyano-3-phenoxy-benzyl (1R,cis) 2,2-dimethyl-3-[(Z) 3-oxo-3-(2,2-difluoroethoxy)-1-propenyl]-cyclopropane-carboxylate 4.7 g of the product of Step D were hydrogenated in the same manner as in Step B of Example 7 and after elution with a 7-3 mixture of n-hexane-isopropyl ether, 3.2 g of (S)α-cyano-3-phenoxy-benzyl (1R,cis) 2,2-dimethyl-3-[(Z) 3-oxo-3-(2,2-difluoroethoxy)-1-propenyl]-cyclopropane-carboxylate were obtained with a specific rotation of $[\alpha]_D^{20} = +44° \pm 2.5$ (c=0.5% in CHCl$_3$)

EXAMPLE 12

(S)α-cyano-3-phenoxy-benzyl (1R,cis) 2,2-dimethyl-3-[(Z) 3-oxo-3-(2,2-dichloroethoxy)-1-propenyl]-cyclopropane-carboxylate

STEP A: Tert.-butyl (1R,cis) 2,2-dimethyl-3-[(Z) 3-oxo-3-(2,2-cichloroethoxy)-1-propenyl]-cyclopropane-carboxylate Using the procedure of Step F of Example 9, 4.8 g of tert.-butyl (1R,cis) 2,2-dimethyl-3-[(Z) 3-hydroxy-3-oxo-1-propenyl]-cycloropane-carboxylate and 2 ml of 2,2-dichloroethanol were reacted to obtain after elution with a 9-1 mixture of cyclohexane-ethyl acetate 5.6 g of tert.-butyl (1R, cis) 2,2-dimethyl-3-[(Z) 3-oxo-3-(2,2-dichloroethoxy)-1-propenyl]-cyclopropane-carboxylate.

STEP B: (1R,cis) 2,2-dimethyl-3-[(Z) 3-oxo-3-(2,2-dichloroethoxy)-1-propenyl]-cyclopropane-carboxylic acid Using the procedure of Step C of Example 11, 5.6 of the product of Step A were reacted to obtain 4.5 g of (1R,cis) 2,2-dimethyl-3-[(Z) 3-oxo-3-(2,2-dichloroethoxy)-1-propenyl]-cyclopropane-carboxylic acid.

STEP C: (S)α-cyano-3-phenoxy-benzyl (1R,cis) 2,2-dimethyl-3-[(Z) 3-oxo-3-(2,2-dichloroethoxy)-1-propenyl]-cyclopropane-carboxylate Using the procedure of Step F of Example 9, 3 g of the product of Step B and 2.25 g of (S)α-cyano-3-phenoxy-benzyl alcohol were reacted to obtain after elution with 8-3 and 9-1 mixtures of cyclohexane-ethyl acetate 1.6 of (S)α-cyano-3-phenoxy-benzyl (1R,cis) 2,2-dimethyl-3-[(Z) 3-oxo-3-(2,2-dichloroethoxy(-1-propenyl]-cyclopropane-carboxylate with a specific rotation of $[\alpha]_D^{20} = +54° \pm 2°$ (c=1% in benzene).

EXAMPLE 13

(RS)α-cyano-(6-phenoxy-2-pyridyl)-methyl (1R,cis) 2,2-dimethyl-3-[(Z) 3-oxo-3-(2,2-difluoroethoxy)-1-propenyl]-cyclopropane-carboxylate Using the procedure of Step F of Example 9, (1R,cis) 2,2-dimethyl-3-[(Z) 3-oxo-3-(2,2-difluoroethoxy)-1-propenyl]-cyclopropane-carboxylic acid prepared as in Example 21 except 2,2-difluoroethanol was used and (RS)α-cyano(6-phenoxy-2-pyridyl)-methanol were reacted to obtain (RS)α-cyano-(6-phenoxy-2-pyridyl)-methyl (1R,cis) 2,2-dimethyl-3-[(Z) 3-oxo-3-(2,2-difluoroethoxy)-1-propenyl]-cyclopropane-carboxylate with a specific rotation of $[\alpha]_D^{20} = +50.5° \pm 2°$ (c=0.8% in chloroform).

EXAMPLE 14

(R)α-cyano-3-phenoxy-benzyl (1R,cis) 2,2-dimethyl-3-[(Z) 3oxo-3-(2,2-difluoroethoxy)-1-propenyl]-cyclopropane-carboxylate Using the procedure of Step F of Example 9, (1R,cis) 2,2-dimethyl-3-[(Z) 3-oxo-3-(2,2-difluoroethoxy)-1-propenyl]-cyclopropane-carboxylic acid and (R)α-cyano-3-phenoxy-benzyl alcohol were reacted to obtain (R)α-cyano-3-phenoxy-benzyl (1R,cis) 2,2-dimethyl-3-[(Z) 3-oxo-3-(2,2-difluoroethoxy)-1-propenyl]-cyclopropane-carboxylate with a specific rotation of $[\alpha]_D^{20} = +117.5° \pm 3°$ (c=0.6% in chloroform).

EXAMPLE 15

[3-propargyl-2,5-dioxo-imidazolidinyl]-methyl (1R,cis) 2,2-dimethyl-3-[(Z) 3-oxo-3-(2,2-difluoroethoxy)-1-propenyl]-cyclopropane-carboxylate Using the procedure of Step F of Example 9, (1R, cis) 2,2-dimethyl-3-[(Z) 3-oxo-3-(2,2-difluoroethoxy)-1-propenyl]-cyclopropane-carboxylic acid and [3-propargyl-2,5-dioxo-imidazolidinyl]-methanol were reacted to obtain [3-propargyl-2,5-dioxo-imidazolidinyl]-methyl (1R,cis) 2,2-dimethyl-3-[(Z) 3-oxo-3-(2,2-difluoroethoxy-1-propenyl]-cyclopropane-carboxylate with a specific rotation of $[\alpha]_D^{20} = +18° \pm 2°$ (c=1% in CHCl$_3$).

EXAMPLE 16

(R)α-ethynyl-3-phenoxy-benzyl (1R,cis) 2,2-dimethyl-3-[(Z) 3-oxo-3-(2,2-difluoroethoxy)-1-propenyl]-cyclopropane-carboxylate Using the procedure of Step F of Example 9, (1R, cis) 2,2-dimethyl-3-[(Z) 3-oxo-3-(2,2-difluoroethoxy)-1-propenyl]-cyclopropane-carboxylic acid and α-ethynyl-3-phenoxy-benzyl alcohol were reacted to obtain (R)α-ethynyl-3-phenoxy-benzyl (1R,cis) 2,2-dimethyl-3-[(Z) 3-oxo-3-(2,2-difluoroethoxy)-1-propenyl]-cyclopropane-carboxylate with a specific rotation of $[\alpha]_D^{20} = +47° \pm 1.5°$ (c=1% in CHCl$_3$).

EXAMPLE 17

(3-propargyl-2,5-dioxo-1-imidazolidinyl)-methyl (1R,cis) 2,2 dimethyl-3-[(Z) 3-oxo-3-(2-fluoroethoxy)-1-propenyl]-cyclopropane-carboxylate Using the procedure of Step F of Example 9, (1R, cis) 2,2-dimethyl-3-[(Z) 3-oxo-3-(2-fluoroethoxy)-1-propenyl cyclopropane-carboxylic acid prepared as in Example 21 except 2-fluoroethanol was used and (3-propargyl-2,5-dioxo-imidazol dinyl)-methanol were reacted to obtain (3-propargyl-2,5-diox -1-imidazolidinyl)-methyl (1R,cis) 2,2-dimethyl-3-[(Z) 3-oxo-3-(2fluoroethoxy)-1-propenyl]-cyclopropane-carboxylate with a specific rotation of $[\alpha]_D^{20} = +18° \pm 2°$ (c=1% in CHCl$_3$)

EXAMPLE 18

(R,S)α-cyano-(6-phenoxy-2-pyridyl)-methyl (1R,cis) 2,2-dimethyl-3-[(Z) 3oxo-3-(2-fluoroethoxy)-1propenyl]-cyclopropane-carboxylate Using the procedure of Step F of Example 9, (1R, cis) 2,2-dimethyl-3-[(Z) 3-oxo-3-(2-fluoroethoxy)-1-propenyl]cyclopropane-1-carboxylic acid and (R,S)α-cyano-[6-phenoxy-2-pyridinyl)-methanol were reacted to obtain (R,S)α-cyano-(6-phenoxy-2-pyridyl)-methyl (1R,cis) 2,2-dimethyl-3-[(Z) 3-oxo-3-(2-fluoroethoxy)-1-propenyl]-cyclopropane-carboxylate with a specific rotation of $[\alpha]_D^{20} = +49.5° \pm 2.5°$ (c=0.5% in CHCl$_3$).

EXAMPLE 19

(R)α-cyano-3-phenoxy-benzyl (1R,cis) 2,2-dimethyl-3-[(Z) 3-oxo-3-(2-fluroethoxy)-1-propenyl]-cyclopropane-carboxylate Using the procedure of Step F of Example 9, (1R, cis) 2,2-dimethyl-3-[(Z) 3-oxo-3-(2-fluoroethoxy)-1-propenyl]cyclopropane-carboxylic acid and (R)α-methyl-3-phenoxy-benzyl alcohol were reacted to obtain (R)α-cyano-3-phenoxy-benzyl (1R,cis) 2,2-dimethyl-3-[(Z) 3-oxo-3-(2-fluoroethoxy)-1-propenyl]-cyclopropane-carboxylate with a specific rotation of $[\alpha]_D^{20} = +123° \pm 1.5°$ (c=1% in CHCl$_3$).

EXAMPLE 20

α-ethynyl-3-phenoxy-benzyl (1R,cis) 2,2-dimethyl-3-[(Z) 3-oxo -3-(2-fluoroethoxy)-1-propenyl]-cyclopropane-carboxylate Using the procedure of Step F of Example 9, (1R, cis) 2,2-dimethyl-3-[(Z) 3-oxo-3-(2-fluoroethoxy)-1-propenyl]-cyclopropane-carboxylic acid and α-ethynyl- 3-phenoxy-benzyl alcohol were reacted to obtain α-ethynyl-3-phenoxy-benzyl (IR,cis) 2,2-dimethyl-3-[(Z) 3-oxo-3-(2-fluoroethoxy) -1-propenyl]-cyclopropane-carboxylate with a specific rotation of $[\alpha]_D^{20} = +47° \pm 1.5°$ (c=1% in CHCl$_3$).

EXAMPLE 21

(R)α-ethynyl-3-phenoxy-benzyl (IR,cis) 2,2-dimethyl-3-[(Z) 3-oxo-3-(2-(1,1,1,3,3,3-hexafluoropropoxy))-1-propenyl]-cyclopropane-carboxylate STEP A: Tert.-butyl (IR,cis) 2,2-dimethyl-3-[(Z) 3-oxo-3-(2-(1,1,1,3,3,3-hexafluoropropoxy))-1-propenyl]-cyclopropane-carboxylate Using the procedure of Step F of Example 9, 3.6 g of tert.-butyl (IR,cis) 2,2-dimethyl-3-[(Z) 3-hydroxy-3-oxo-1 propenyl]-cyclopropane-carboxylate and 3 g of hexafluoroiso-propanol were reacted to obtain after elution with a 4–6 mixture of benzene-cyclohexane 4.9 g of tert.-butyl (IR,cis) 2,2-dimethyl-3-[(Z) 3-oxo-3-(2-(1,1,1,3,3,3-hexafluoropropoxy))-1-propenyl]-cyclopropane-carboxylate melting at 92° C. STEP B: (IR,cis) 2,2-dimethyl-3-[(Z) 3-oxo-3-(2-(1,1,1,3,3,3-hexafluoropropoxy)) -1-propenyl]-cyclopropane-carboxylic acid Using the procedure of Step C of Example 11, 4.9 g of the product of Step A were reacted to obtain 4.2 g of (IR,cis) 2,2-dimethyl-3-[(Z) 3-oxo-3-(2-(1,1,1,3,3,3-hexafluoropropoxy)) -1-propenyl]-cyclopropane-carboxylic acid.

IR Spectrum (CHCl$_3$):

Absorption at 3500 cm$^{-1}$ (OH of monoacid and dimer); at 1755 cm$^{-1}$ shoulder and 1744 cm$^{-1}$ maxi (conjugated ester carbonyl); at 1695 cm$^{-1}$ (acid); at 1627 cm$^{-1}$ conjugated C=C); at 1380 cm$^{-1}$ shoulder (gem. dimethyls).

STEP C: (R)α-ethynyl-3-phenoxy-benzyl (IR,cis) 2,2-dimethyl -3-[(Z) 3-oxo-3-(2-(1,1,1,3,3,3-hexafluoropropoxy))-1-propenyl]cyclopropane-carboxylate Using the procedure of Step F of Example 9, the product of Step B and (R)α-ethynyl-3-phenoxy-benzyl alcohol were reacted to obtain (R)α-ethynyl-3-phenoxy-benzyl (IR,cis) 2,2-dimethyl-3-[(Z) 3-oxo-3-(2-(1,1,1,3,3,3-hexafluoropropoxy) -1-propenyl]-cyclopropane-carboxylate with a specific rotation of $[\alpha]_D^{20} = +31.5° \pm 1.5°$ (c=1% in CHCl$_3$).

EXAMPLE 22

(R)α-methyl-3-phenoxy-benzyl (IR,cis) 2,2-dimethyl-3-[(Z) 3-oxo-3-(2-(1,1,1,3,3,3-hexafluoropropoxy))-1-propenyl]-cyclopropane-carboxylate Using the procedure of Step F of Example 9, the acid of Step B of Example 21 and (R) α-methyl-3-phenoxy-benzyl] alcohol were reacted to obtain (R)α-methyl-3-phenoxyl-benzyl (IR,cis) 2,2-dimethyl-3-[(Z) 3-oxo-3-(2-(1,1,1,3,3,3-hexafluoropropoxy)) -1-propenyl]-cyclopropane-carboxylate with a specific rotation of $[\alpha]_D^{20} = +97° \pm 2°$ (c=1% in CHCl$_3$).

EXAMPLE 23

(S)α-cyano-3-phenoxy-benzyl (IR,cis) 2,2-dimethyl-3-[(Z) 3-oxo -3-(2-(1,1,1,3,3,3-hexafluoropropoxy))-1-propenyl]-cyclopropane-carboxylate Using the procedure of Step F of Example 9, the acid of Step B of Example 21 and (S)α-cyano-3-phenoxy-benzyl alcohol were reacted to obtain (S)α-cyano-3-phenoxy-benzyl (IR,cis) 2,2-dimethyl-3-[(Z) 3-oxo-3-(2-(1,1,1,3,3,3-hexafluoropropoxy)) -1-propenyl]-cyclopropane-carboxylate with a specific rotation of $[\alpha]_D^{20} = +23.5° \pm 2°$ (c=0.5% in benzene)

EXAMPLE 24

3,4,5,6-tetrahydrophthalimidomethyl (IR,cis) 2,2-dimethyl-3-[(Z) 3-oxo-3-(2-(1,1,1,3,3,3-hexafluorophenoxy))-1-propenyl]-cyclopropane-carboxylate Using the procedure of Step F of Example 9, the acid of Step B of Example 21 and 3,4,5,6-tetrahydrophthalimidomethanol were reacted to obtain 3,4,5,6-tetrahydrophthalimidomethyl (IR,cis) 2,2-dimethyl-3-[(Z) 3-oxo-3-(2-(1,1,1,3,3,3-hexafluorophenoxy)) -1-propenyl]-cyclopropane-carboxylate with a specific rotation of $[\alpha]_D^{20} = -30° \pm 1°$ (c=1% in CHCl$_3$).

EXAMPLE 25

(R,S) cyano-(6-phenoxy-2-pyridyl)-methyl (IR,cis) 2,2-dimethyl -3-[(Z) 3-oxo-3-(2-(1,1,1,3,3,3-hexafluoropropoxy))-1-propenyl]-cyclopropane-carboxylate Using the procedure of Step F of Example 9, the acid of Step B of Example 21 & (R,S) cyano-(6-phenoxy-2-pyridyl)-methanol were reacted to obtain (R,S) cyano-(6-phenoxy-2-pyridyl)-methyl (IR,cis) 2,2-dimethyl-3-[(Z) 3-oxo-3-(2-(1,1,1,3,3,3-hexafluoropropoxy)) -1-propenyl]-cyclopropane-carboxylate with a specific rotation of $[\alpha]_D^{20} = +33.5° \pm 2.5°$ (c=0.2% in CHCl$_3$).

EXAMPLE 26

[3-propargyl-2,5-dioxo-imidazolidinyl]-methyl (IR,cis) 2,2-dimethyl -3-[(Z) 3-oxo 3-(2,2,2-trifluoroethoxy)-1-propenyl]-cyclopropane-carboxylate Using the procedure of Step F of Example 9, the acid of Step D of Example 1 and (3-propargyl-2,5-dioxo-imidazolidinyl)-methanol were reacted to obtain [3-propargyl-2,5-dioxo-imidazolidinyl]-methyl (IR, cis) 2,2-dimethyl-3-[(Z) 3-oxo 3-(2,2,2-trifluoroethoxy) -1-propenyl]-cyclopropane-carboxylate with a specific rotation of $[\alpha]_D^{20} = -4° \pm 1°$ (c=1% in benzene). EXAMPLE 27

(R)α-methyl-3-phenoxy-benzyl (IR,cis) 2,2-dimethyl-3-[(Z) 3-oxo-3-(2,2,2-trifluoroethoxy)-1-propenyl]-cyclopropane-carboxylate Using the procedure of Step F of Example 9, the acid of Step D of Example 1 and (R)α-methyl-3-phenoxy-benzyl alcohol were reacted to obtain (R)α-methyl-3-phenoxy-benzyl (IR,cis) 2,2-dimethyl-3-[(Z) 3-oxo-3-(2,2,2-trifluoroethoxy) -1-propenyl]-cyclopropane-carboxylate with a specific rotation of $[\alpha]_D^{20} = +108.5° \pm 2°$ (c=1% in CHCl$_3$).

EXAMPLE 28

3,4,5,6-tetrahydrophthalimidomethyl (IR,cis) 2,2-dimethyl-3-[(Z) 3-oxo-3-(2,2,2-trifluoroethoxy)-1-propenyl]-cyclopropane-carboxylate Using the procedure of Step F, of Example 9, the acid of Step D of Example 1 and 3,4,5,6-tetrahydrophthalimidomethanol were reacted to obtain 3,4,5,6-tetrahydrophthalimidomethyl (IR,cis) 2,2-dimethyl-3-[(Z) 3-oxo-(2,2,2-trifluoromethoxy) -1-propenyl]-cyclopropane-carboxylate with a specific rotation of $[\alpha]_D^{20} = +2.5° \pm 2°$ (c=0.5% in CHCl$_3$).

EXAMPLE 29

(R)α-ethynyl-3-phenoxy-benzyl (IR,cis) 2,2-dimethyl-3-[(Z) 3-oxo -3-(2,2,2-trifluoroethoxy)1-propenyl]-cyclopropane-carboxylate Using the procedure of Step F of Example 9, the acid of Step D of Example 1 and (R)α-ethynyl-3-phenoxy-benzyl alcohol were reacted to obtain (R)α-ethynyl-3-phenoxy-benzyl (IR,cis) 2,2-dimethyl-3[(Z) 3-oxo-3(2,2,2-trifluoroethoxy)-1-propenyl]-cyclopropane-carboxylate with a specific rotation of $[\alpha]_D^{20} = +42° \pm 1.5°$ (c=1% in CHCl$_3$).

EXAMPLE 30

(R,S)α-cyano-(6-phenoxy-2-pyridyl)-methyl (IR,cis) 2,2-dimethyl -3-[(Z) 3-oxo-3-(2,2,2-trifluoroethoxy)-1-propenyl]-cyclopropane-carboxylate Using the procedure of Step F of Example 9, the acid of Step D of Example 1 and (R,S)α-cyano-(6-phenoxy-2-pyridyl)-methanol were reacted to obtain (R,S)α-cyano-(6-phenoxy-2-pyridyl)-methyl (IR,cis) 2,2-dimethyl-3-[(Z) 3-oxo -3-(2,2,2-trifluoroethoxy)-1-propenyl]-cyclopropane-carboxylate with a specific rotation of $[\alpha]_D^{20} = +46.5° \pm 2°$ (c=0.7 in CHCl$_3$).

EXAMPLE 31

(S)α-cyano-3-phenoxy-benzyl (IR,cis) 2,2-dimethyl-3-[(Z) 3-oxo-3-(2,2,2-trichloroethoxy)-1-propenyl]-cyclopropane-carboxylate

STEP A: (S)α-cyano-3-phenoxy-benzyl (IR,cis) 2,2-dimethyl-3 [(Z) 3-hydroxy-3-oxo-1-propenyl]-cyclopropane-carboxylate A mixture of 4.7 g of (S)α-cyano-3-phenoxy-benzyl (IR,cis) 2,2-dimethyl-3-(2-carboxyethynyl)-cyclopropane-carboxylate in 45 ml of ethyl acetate was hydrogenated in the presence of 500 mg of 10% palladium hydroxide on barium sulfate and 6.5 ml of quinoline and the mixture was filtered. The filtrate was washed with N hydrochloric acid, then with water until neutral, dried and evaporated to dryness. The 5.1 g of oil residue were chromatographed over silica gel and eluted with a 70-30-1 mixture of hexane-ethyl acetate-acetic acid to obtain 3.8 g of (S)α-cyano-3-phenoxy-benzyl (IR,cis) 2,2-dimethyl-3-[(Z) 3-hydroxy-3-oxo-1-propenyl]-cyclopropane-carboxylate.

STEP B: (S)α-cyano-3-phenoxy-benzyl (IR,cis) 2,2-dimethyl-3-[(Z) 3-oxo-3-(2,2,2-trichloroethoxy)-1-propenyl]-cyclopropane-carboxylate Using the procedure of Step F of Example 9, the ester of Step A after reaction with 2,2,2-trichloroethanol and (S)α-cyano-3-phenoxy-benzyl alcohol was reacted to obtain (S)α-cyano-3-phenoxy-benzyl (IR,cis) 2,2-dimethyl-3-[(Z) 3-oxo-3-(2,2,2-trichloroethoxy)-1-propenyl]-cyclopropane-carboxylate with a specific rotation of $[\alpha]_D^{20} = +42.5° \pm 2°$ (c=0.5% in benzene).

EXAMPLE 32

(S)α-cyano-3-phenoxy-benzyl (IR,cis) 2,2-dimethyl-3-[(Z) 3-oxo -3-(2-chloroethoxy)-1-propenyl]-cyclopropane-carboxylate Using the procedure of Step F of Example 9, the ester of Step A of Example 31 after reaction with 2-chloroethanol and (S)α-cyano-3-phenoxy-benzyl alcohol was reacted to obtain (S)α-cyano-3-phenoxy-benzyl (IR,cis) 2,2-dimethyl -3-[(Z) 3-oxo-3-(2-choloroethoxy)-1-propenyl]-cyclopropane-carboxylate with a specific rotation of $[\alpha]_D^{20} = +39° \pm 4°$ (c=0.25% in benzene).

EXAMPLE 33

(S)α-cyano-3-phenoxy-benzyl (IR,cis) 2,2-dimethyl-3-[(Z) 3-oxo -3-(2-methoxyethoxy)-1-propenyl]-cyclopropane-carboxylate Using the procedure of Step F of Example 9, the ester of Step A of Example 31 after reaction with 2-methoxyethanol and (S)α-cyano-3-phenoxy-benzyl alcohol was reacted to obtain (S)α-cyano-3-phenoxy-benzyl (IR,cis) 2,2-dimethyl -3-[(Z) 3-oxo-3-(2-methoxyethoxy)-1-propenyl]-cyclopropane-carboxylate with a specific rotation of $[\alpha]_D^{20} = +37.5° \pm 2°$ (c=1% in CHCl$_3$).

EXAMPLE 34

(S)α-cyano-3-phenoxy-benzyl-(IR,cis) 2,2-dimethyl-3-[(Z) 3-oxo-3-(R,S)-(1-cyanoethoxy)-1-propenyl]-cyclopropane-carboxylate Using the procedure of Step F of Example 9, the ester of Step A of Example 31 after reaction with 1-cyanoethanol and (S)α-cyano-3-phenoxy-benzyl alcohol was reacted to obtain (S)α-cyano-3-phenoxy-benzyl-(IR,cis) 2,2-dimethyl-3-[(Z) 3-oxo-3-(R,S)-(1-cyanoethoxy)-1-propenyl]-cyclopropane-carboxylate with a specific rotation of $[\alpha]_D^{20} = +64.5° \pm 3°$ (c=0.3% in CHCl$_3$).

EXAMPLE 35

(S)α-cyano-3-phenoxy-benzyl (IR,cis) 2,2-dimethyl-3-[(Z) 3-oxo -3-(2-fluoroethoxy)-1-propenyl]-cyclopropane-carboxylate Using the procedure of Step F of Example 9, the ester of Step A of Example 31 after reaction with 2-fluoroethanol and (S)α-cyano-3-phenoxy-benzyl alcohol was reacted to obtain (S)α-cyano-3-phenoxy-benzyl (IR,cis) 2,2-dimethyl -3-[(Z) 3-oxo-3-(2fluoroethoxy)-1-propenyl]-cyclopropane-carboxylate with a specific rotation of $[\alpha]_D^{20} = +48°$ (c=0.25% in benzene).

EXAMPLE 36

(S)α-cyano-3-phenoxy-benzyl (IR,cis) 2,2-dimethyl-3-[(Z) 3-oxo -3-phenethoxy-1-propenyl]-cyclopropane-carboxylate Using the procedure of Step F of Example 9, the ester of Step A of Example 31 after reaction with phenethanol and (S)α-cyano-3-phenoxy-benzyl alcohol was reacted to obtain (S) -cyano-3-phenoxy-benzyl (IR,cis) 2,2-dimethyl-3[(Z) 3-oxo -3-phenethoxy-1-propenyl]-cyclopropane-carboxylate with a specific rotation of $[\alpha]_D^{20} = +46° \pm 2.5°$ (c=0.5% in benzene).

EXAMPLE 37

(S)α-cyano-3-phenoxy-benzyl (IR,cis) 2,2-dimethyl-3[(Z) 3-oxo 3-(2,2-dimethyldioxolanyl-4-(RS)-methoxy)-1-propenyl]-cyclopropane-carboxylate Using the procedure of Step F of Example 9, the ester of Step A of Example 31 after reaction with (2,2-dimethyldioxolanyl)-4-(R,S)-methanol and (S)α-cyano-3-phenoxy-benzyl alcohol was reacted to obtain (S)α-cyano-3-phenoxy-benzyl (IR,cis) 2,2-dimethyl-3-[(Z) 3-oxo-3-(2,2-dimethyl-dioxolanyl -4-(RS)-methoxy)-1-propenyl]-cyclopropane-carboxylate with a specific rotation of $[\alpha]_D^{20} = +46° \pm 2°$ (c=0.75% in benzene).

EXAMPLE 38

(R,S) α-cyano-3-phenoxy-benzyl (IR,cis) 2,2-dimethyl-3-[(Z) 3-oxo-3-(2-dimethylaminoethoxy)-1-propenyl]-cyclopropane-carboxylate Using the procedure of Step A of Example 31, (R,S) α-cyano-3-phenoxy-benzyl (IR,cis) 2,2-dimethyl-3-[(Z) 3-oxo -3-hydroxy-1-propenyl]-cyclopropane-carboxylate was prepared and was then reacted with 2-dimethylamino-ethanol to obtain (R,S)α-cyano-3-phenoxy-benzyl (IR,cis) 2,2-dimethyl-3-[(Z) 3-oxo-3-(2-dimethylaminoethoxy)-1-propenyl]-cyclopropane-carboxylate with a specific rotation of $[\alpha]_D^{20} = +23° \pm 3°$ (c=0.25% in CHCl$_3$).

EXAMPLE 39

(R)α-methyl-3-phenoxy-benzyl (IR,cis) 2,2-dimethyl-3-[(Z) 3-oxo-3-(2-methoxyethoxy)-1-propenyl]-cyclopropane-carboxylate STEP A: (R)α-methyl-3-phenoxy-benzyl (IR,cis) 2,2-dimethyl -3-[3-oxo-3-(2,2,2-trichloroethoxy)-1-propynyl]-cyclopropane-carboxylate Using the procedure of Step D of Example 9, 6 g of (IR,cis) 2,2-dimethyl-3-[3-oxo-3-(2,2,2-trichloroethoxy) -1-propynyl]-cyclopropane-carboxylic acid and 4.1 g of 1-(R) (3-phenoxy-phenyl)-ethanol were reacted to obtain after chromatography and elution with an 8–2 mixture of cyclohexane-ethyl acetate 4.38 g of (R)α-methoxy-3-phenoxy-benzyl (IR, cis) 2,2-dimethyl-3-[3-oxo-3-(2,2,2-trichloroethoxy)-1-propynyl]-cyclopropane-carboxylate.

STEP B: (R)α-methyl-3phenoxy-benzyl (IR,cis) 2,2-dimethyl-3[3-oxo -3-hydroxy-1-propynyl]-cyclopropane-carboxylate A solution of 4.16 g of the product of Step A in 4 ml of methylene chloride was admixed with 45 ml of acetic acid containing 10% of water and 0.53 g of zinc powder and the mixture was stirred for 30 minutes at room temperature, then another 0.53 g of zinc powder were added 4 times until The reaction was complete and after 3 hours contact, the mixture was filtered. The filtrate was extracted with methylene chloride and the organic phase was washed with water, dried and evaporated to dryness by azeotropic distillation with toluene to obtain 3.05 g of (R)α-methyl-3-phenoxy-benzyl (IR,cis) 2,2-dimethyl-3-[3-oxo-3-hydroxy-1-propynyl]-cyclopropane-carboxylate.

STEP C: (R)α-methyl-3- phenoxy-benzyl (IR, cis) 2,2-dimethyl 3-[(Z) 3-hydroxy-3-oxo-1-propenyl]-cyclopropane-carboxylate Using the procedure of Step B of Example 7, the product of Step B was reacted to obtain 2.9 g of crude (R)α-methyl-3-phenoxy-benzyl (IR,cis) 2,2-dimethyl-3-[(Z) 3-hydroxy -3-oxo-1-propenyl]-cyclopropane-carboxylate which was used as is for the next step.

STEP D: (R)α-methyl-3-phenoxy-benzyl (IR,cis) 2,2-dimethyl -3-[(Z) 3-oxo-3-(2-methoxyethoxy)-1-propenyl]-cyclopropane-carboxylate The product of Step C was reacted with 2-methoxyethanol to obtain (R)α-methyl-3-phenoxy-benzyl (IR,cis) 2,2-dimethyl-3-[(Z) 3-oxo-3-(2-methoxyethoxy)-1-propenyl]-cyclopropane-carboxylate.

NMR Spectrum (deuterochloroform):

Peaks at 1.22–1.25 ppm (hydrogens of geminal methyls); at 1.45–1.55 ppm (hydrogens of —CH$_3$ of 1-ester of cyclopropane); at 5.7 to 6.0 ppm (hydrogens of benzyl); at 3.42 ppm (hydrogens of —OCH$_3$); at 4.22 to 4.38 ppm (1-hydrogens of 3-ester of cyclopropane); at 3.55 to 3.72 ppm (2-hydrogens of 3-ester of cyclopropane); at 5.85–6.05 ppm and 6.32 to 6.8 ppm (ethylenic hydrogens).

EXAMPLE 40

(S)α-cyano-3-phenoxy-benzyl (IR,cis) 2,2-dimethyl-3-[(Z) 3-oxo-3-(1-methoxy-1-trifluoromethylethoxy)-1-propenyl]-cyclopropane-carboxylate Under inert atmosphere, a mixture of 1.02 g of (S)α-cyano-3-phenoxy-benzyl (IR,cis) 2,2-dimethyl-3-[(Z) 3-chloro-3-oxo-1-propenyl)-cyclopropane-carboxylate prepared by reaction of thionyl chloride and (S)α-cyano-3-phenoxy-benzyl (IR,cis) 2,2-dimethyl-3-[(Z) 3hydroxy-3-oxo-1propenyl]-cyclopropane-carboxylate and 9 ml of methylene chloride were stirred and 1.12 g of 1-methyl-1-trifluoromethyl-ethanol were added thereto. The mixture was stirred for 48 hours at room temperature and was then evaporated to dryness under reduced pressure. The residue was chromatographed over silica gel and eluted with a 8–2 mixture of hexane-ethyl ether to obtain 250 mg of (S)α-cyano-3-phenoxy-benzyl (IR,cis) 2,2-dimethyl 3-[(Z) 3-oxo-3-(1-methoxy-1-trifluoromethylethoxy)-1-propenyl]-cyclopropane-carboxylate with a melting point of 59° C. and a specific rotation of $[\alpha]_D^{20} = +57° \pm 2°$ (c=0.4% in benzene).

EXAMPLE 41

(S)α-cyano-3-phenoxy-benzyl (IR,cis) 2,2-dimethyl-3-[(Z) 3-oxo-3-(1-trifluoromethyl-1methyl-propyloxy)-1-propenyl]-cyclopropane-carboxylate 900 mg of (S)α-cyano-3-phenoxy-benzyl (IR,cis) 2,2-dimethyl-3-[(Z) 3-chloro-3-oxo-1-propenyl]-cyclopropane carboxylate were dissolved in 3 ml of methylene chloride and 1 ml of 1-trifluoromethyl-1-methyl propanol was added thereto. The mixture was stirred for 16 hours at room temperature under inert atmosphere and away from humidity. After 3 days at room temperature, the reaction mixture was washed with a saturated aqueous solution of sodium bicarbonate, then with water, dried and evaporated to dryness. The residue was chromatographed over silica gel and eluted with a 8–2 mixture of hexane-ethyl ether to obtain 570 mg of (S)α-cyano-3-phenoxy-benzyl (IR,cis) 2,2-dimethyl-3-[(Z) 3-oxo-3-(1-trifluoromethyl-1-methyl-propyloxy) -1-propenyl]-cyclopropane-carboxylate.

EXAMPLE 42

(S)α-cyano-3-phenoxy-benzyl (IR,cis) 2,2-dimethyl-3-[(Z) 3-oxo-3-(2,3-dihydroxypropyloxy)-1-propenyl]-cyclopropane-carboxylate.

A mixture of 4.65 g of (S)α-cyano-3-phenoxy-benzyl (IR,cis) 2,2-dimethyl-3-[(Z) 3-oxo-3-(2,2-dimethyl-dioxolanyl -4-(RS)-methoxy-1-propenyl]-cyclopropane-carboxylate, 46 ml of dioxane, 9 ml of water and 0.45 g of p-toluene sulfonic acid was refluxed for 45 minutes and the majority of the dioxane was distilled off at 40° C. under reduced pressure. The residue was taken up in 150 ml of methylene chloride and 25 ml of water and the mixture was stirred and decanted. The organic phase was washed with water, dried and evaporated to dryness under reduced pressure. The residue was chromatographed over silica gel and eluted with a 3–7 mixture of cyclohexane-ethyl acetate to obtain 3.85 g of (S)α-cyano-3-phenoxy-benzyl (IR,cis) 2,2-dimethyl-3-[(Z) 3-oxo-3-(2,3-dihydroxy-propyloxy) -1-propenyl]-cyclopropane-carboxylate with a specific rotation of $[\alpha]_D^{20} = +53° \pm 2.5°$ (c=0.5% in CHCl$_3$).

EXAMPLE 43

(RS)α-cyano-3-phenoxy-benzyl (IR,cis) 2,2-dimethyl-3-[(Z) 3-oxo-3-(2-tetrahydropyranyloxyethoxy)-1-propenyl]-cyclopropane-carboxylate STEP A: (RS)α-cyano-3-phenoxy-benzyl (IR,cis) 2,2-dimethyl -3-[(Z) 3-oxo-3-(2-tetrahydropyranyloxyethoxy)-1-propynyl]-cyclopropane-carboxylate Using the procedure of Step A of Example 7, 2.3 g of (RS)α-cyano-3-phenoxy-benzyl (IR,cis) 2,2-dimethyl-3[(Z) 3-hydroxy-3-oxo-1-propynyl]-cyclopropane-carboxylaae and 7.5 g of 1-bromo-2-(2-tetrahydropyranyl)-oxyethane were reacted to obtain 1.8 g of (RS)α-cyano-3-phenoxy-benzyl (IR,cis) 2,2-dimethyl -3-[(Z) 3-oxo-3-(2-tetrahydropyranyloxyethoxy)-1-propynyl) -cyclopropane-carboxylate after chromatography over silica gel and elution with a 3–1 mixture of cyclohexane-ethyl acetate.

STEP B: (RS)α-cyano-3-phenoxy-benzyl (IR,cis) 2,2-dimethyl -3-[(Z) 3-oxo-3-(2-tetrahydropyranyloxyethoxy)-1-propenyl]-cyclopropane-carboxylate Using the procedure of Step B of Example 7, product of Step A was reacted to obtain after purification by chromatography and elution with an 8–2 mixture of cyclohexane-ethyl acetate, 1.3 g of (RS)α-cyano-3-phenoxy-benzyl (IR,cis) 2,2-dimethyl-3-[(Z) 3-oxo-3-(2-tetrahydropyranyloxyethoxy)-1-propenyl]-cyclopropane-carboxylate with a specific rotation of $[\alpha]_D^{20} = +33° \pm 1°$ (c=1% in CHCl$_3$).

EXAMPLE 44

(RS)α-cyano-3-phenoxy-benzyl (IR,cis) 2,2-dimethyl-3-[(Z) 3-oxo -3-(2-hydroxyethoxy)-1-propenyl]-cyclopropane-carboxylate A mixture of 0.85 g of the product of Example 43, 17 ml of ethanol, 5 ml of dioxane, 1 ml of water and 4 ml of 2N hydrochloric acid was stirred at 20° C. for 3 hours and 1 ml of triethylamine was then added thereto. The mixture was evaporated to dryness and the residue was taken up with a water/ice mixture. The mixture was extractd with methylene chloride and the organic phase was washed with water, dried and evaporated to dryness. The residue was chromatographed over silica gel and eluted with a 65–35 mixture of cyclohexaneethyl acetate to obtain 0.65 g of (RS)α-cyano-3-phenoxy-benzyl (IR,cis) 2,2-dimethyl-3-[(Z) 3-oxo-3-(2-hydroxyethoxy)-1-propenyl]-cyclopropane-carboxylate having a specific rotation of $[\alpha]_D^{20} = +42.5° \pm 2.5°$ (c=0.5% in CHCl$_3$).

EXAMPLE 45

3-phenoxy-benzyl alcohol and (IR,cis) 2,2-dimethyl -3-[(Z) 3-oxo-3-(1,1,1,3,3,3-hexafluoropropoxy)1-1-propenyl]-cyclopropane-carboxylic acid were reacted to obtain 3-phenoxy-benzyl (IR,cis) 2,2-dimethyl-3-[(Z) 3-oxo-3-(1,1,1,3,3,3-hexafluoropropoxy) -propenyl]-cyclopropane-carboxylate with a specific rotation of $[\alpha]_D^{20} = +26.5° \pm 2.5°$ (c=0.5% in CHCl$_3$).

EXAMPLE 46

(S)α-cyano-3-phenoxy-4-fluoro-benzyl alcohol and (IR,cis) 2,2-dimethyl-3-[(Z) 3-oxo-3-(1,1,1,3,3,3-hexafluoropropoxy) -1-propenyl]-cyclopropane-carboxylic acid were reacted to obtain (S)α-cyano-3-phenoxy-4-fluoro-benzyl (IR,cis) 2,2-dimethyl-3-[(Z) 3-oxo-3-(1,1,1,3,3,3-hexafluoropropoxy-1-propenyl]-cyclopropane-carboxylate with a specific rotation of $[\alpha]_D^{20} = +27° \pm 2°$ (c=0.8% in benzene).

EXAMPLE 47

(S)α-cyano-3-phenoxy-benzyl (IR,cis,Z) 2,2-dimethyl-3-[3-oxo -3-(2,2-dichloro-1-cyanovinyloxy)-1-propenyl]-cyclopropane-carboxylate 140 mg of 4-dimethylaminopyridine and then 1.76 g of dicyclohexylcarbodiimide were added at 0° C. to a mixture of 3.36 g (S)α-cyano-3-phenoxy-benzyl (IR,-cis,Z) 2,2-dimethyl-3-[3-oxo-3-hydroxy-1-propenyl]-cyclopropane-carboxylate, 1.7 g of chloral cyanohydrin and 16 ml of methylene chloride and the mixture was stirred at 20° C. for 2½ hours and was then evaporated to dryness under reduced pressure. The residue was chromatographed over silica gel and eluted with an 85–15 cyclohexane-ethyl acetate mixture to obtain 1.65 g of (S)α-cyano -3-phenoxy-benzyl (IR,cis,Z) 2,2-dimethyl-3-[3-oxo-3-(2,2-dichloro-1-cyanovinyloxy)-1-propenyl]-cyclopropane-carboxylate with a specific rotation of $[\alpha]_D^{20} = +40°$ (c=0.3% in chloroform).

EXAMPLE 48

(S)α-cyano-3-phenoxy-benzyl (IR,cis,Z) 2,2-dimethyl-3-[3-oxo -3-(RS 1,1,1-trichloropropyl-2-oxy)-1-propenyl]-cyclopropane-carboxylate STEP A: (S)α-cyano-3-phenoxy-benzyl (IR,cis,Z) 2,2-dimethyl -3-[3-oxo-3-chloro-1-propenyl)-cyclopropane-carboxylate A solution of 0.25 ml of 1-chloro-N,N,2-trimethyl-propenylamine, 7.5 ml of methylene chloride and 1.5 ml of tert.-butanol was added to a solution of 0.5 g of (S)α-cyano -3-phenoxy-benzyl (IR,cis,Z) 2,2-dimethyl-3-[3-oxo-3-hydroxy -1-propenyl]-cyclopropane-carboxylate in 7.5 ml of methylene chloride and the mixture was stirred at 20° C. for 48 hours. The mixture was extracted with methylene chloride and the organic phase was washed with water and evaporated to dryness under reduced pressure. The residue was chromatographed over silica gel and was eluted with an 8–2 hexane-ether mixture to obtain 0.43 g of (S)α-cyano-3-phenoxy-benzyl (IR,cis,Z) 2,2-dimethyl -3-[3-oxo-3-chloro-1-propenyl]-cyclopropane-carboxylate melting at 86° C.

STEP B: (S)α-cyano-3-phenoxy-benzyl (IR,cis,Z) 2,2-dimethyl -3-[3-oxo-3-(RS 1,1,1-trichloropropyl-2-oxy)-1-propenyl]-cyclopropane-carboxylate 5.6 g of trichloro isopropanol were added to a solution of 3.52 g of the product of Step A in 15 ml of methylene chloride and the mixture was stirred for 19 hours at 20° C. and was then poured into iced monosodium phosphate solution. The mixture was extracted with methylene chloride and the organic phase was washed with water and evaporated to dryness under reduced pressure. The residue was chromatographed over silica gel and was eluted with an 85–15 cyclohexane-ethyl acetate mixture to obtain 2.85 g of (S)α-cyano -3-phenoxy-benzyl (IR,cis,Z) 2,2-dimethyl-3-[3-oxo-3-(RS 1,1, 1-trichloropropyl-2-oxy)-1-propenyl]-cyclopropane-carboxylate melting at 78° C. and having a specific rotation of $[\alpha]_D^{20} = +50°$ (c=1% in chloroform).

EXAMPLE 49

α-cyano-3-phenoxy-benzyl (IR,cis,Z) 2,2-dimethyl-3-[3-oxo -3-(tetrahydropyran-2-yloxy)-1-propenyl]-cyclopropane-carboxylate A methanolic N hydrochloric acid solution was added dropwise at 15° C. with stirring to a mixture of 1.5 g of α-cyano-3-phenoxy-benzyl (IR,cis,Z) 2,2-dimethyl-3-[3-oxo-3-hydroxy -1-propenyl]-cyclopropane-carboxylate solvated with one mole of acetic acid, 4.5 ml of dihydropyran and 10 ml of methylene chloride and the mixture was stirred at room temperature for 30 minutes. Calcium carbonate was added to the mixture which was then filtered. The filtrate was evaporated to dryness under reduced pressure and the residue was chromatographed over silica gel. Elution with an 8–2 hexane-ether mixture yielded 1.07 g of α-cyano-3-phenoxy-benzyl (IR,cis,Z) 2,2-dimethyl-3-[3-oxo-3-(tetrahydropyran-2-yloxy) -1-propenyl]-cyclopropane-carboxylate with a specific rotation of $[\alpha]_D^{20} = +47°$ (c=0.5% in benzene).

EXAMPLE 50

Using the procedure of Example 49, 4,5-dihydrofuran was reacted to obtain α-cyano-3-phenoxy-benzyl (IR,cis,Z) 2,2-dimethyl -3-[3-oxo-3-(tetrahydrofuran-2-yloxy)-1-propenyl]-cyclopropane-carboxylate with a specific rotation of $[\alpha]_D^{20} = +42.5°$ (c=1% in benzene).

EXAMPLE 51

Using the procedure of Example 47, trifluoroisopropanol was reacted to obtain a mixture of (S)α-cyano-3-phenoxy-benzyl (IR,cis,Z) 2,2-dimethyl-3-[3-oxo-3-(RS 1,1,1-trifluoropropyl-2-oxy) -1-propenyl]-cyclopropane carboxylate which was separated by chromatography over silica gel and elution with a 9–1 cyclohexane-ethyl acetate mixture into an isomer R or S called isomer A melting at 74° C. and having a specific rotation of $[\alpha]_D^{20} = 30\ 34°$ (c=0.6% in chloroform) and a second isomer S or R called isomer B melting at >40° C. and having a specific rotation of $[\alpha]_D^{20} = +44°$ (c=0.5% in chloroform).

EXAMPLE 52

(S)α-cyano-3-phenoxy-benzyl (IR,cis,Z and E) 2,2-dimethyl-3-[3-oxo-3-bromomethoxy-1-propenyl]-cyclopropane-carboxylate 0.1 ml of pyridine and then 1.8 ml of phosphorous tribromide were added at −10° C. to a solution of 5.4 g of (S)α-cyano-3-phenoxy-benzyl (IR,cis,Z) 2,2-dimethyl-3-[3-oxo -3-hydroxy-1-propenyl]-cyclopropane-carboxylate in 18 ml of toluene and the mixture was stirred at 5° C. for 16 hours and was rapidly poured into iced water with stirring. The decanted organic phase was evaporated to dryness under reduced pressure to obtain 4.62 g of product. A mixture of 3.7 g of the said product, 330 mg of formaldehyde and 100 mg of zinc bromide was heated at 50° C. for one hour and was cooled and chromatographed over silica gel. Elution with an 8–2 cyclohexane-ethyl acetate mixture yielded 300 mg of (S)α-cyano-3-phenoxy-benzyl (IR,cis,Z) 2,2-dimethyl-3-[3-oxo-3-bromomethoxy -1-propenyl]-cyclopropane-carboxylate and 1 g of the corresponding E isomer, with a specific rotation of $[\alpha]_D^{20} = -18.5°$ (c=1.2% in chloroform).

NMR Spectrum (deuterochloroform):

Z isomer: Peaks at 1.27–1.31 ppm (hydrogens of geminal methyls); at 1.99–2.13 ppm (1-hydrogen of cyclopropyl); at 3.2–3.5 ppm (3-hydrogen of cyclopropyl); at 5.8–5.9 ppm and 5.51–6.01 ppm (hydrogens of BrCH$_2$O); at 5.9–6.1 ppm (2′ hydrogen of ethylenic); at 6.4 ppm (hydrogen on carbon attached to —CN); at 6.6–6.95 ppm (1′-hydrogen of ethylenic); at 6.95–7.6 ppm (aromatic hydrogens).

E isomer: Peaks at 1.26–1.3 ppm (hydrogens of geminal methyls); at 1.92–2.17 ppm (1- and 3-hydrogens of cyclopropyl); at 5.9 ppm (hydrogens of BrCH$_2$O—); at 5.9–6.2 ppm (2′-hydrogen of ethylenic); at 6.5 ppm (hydrogen on carbon attached to —CN); at 7.0–7.7 ppm (1′-hydrogen of ethylenic); at 7.0–7.7 ppm (aromatic hydrogens).

EXAMPLE 53

(S)α-cyano-3-phenoxy-4-fluoro-benzyl (1R,cis,Z) 2,2-dimethyl -3-[3-oxo-3-(RS 1,1,1-trifluoropropyl-2-oxy)-1-propenyl]-cyclopropane-carboxylate STEP A: (S)α-cyano-3-phenoxy-4-fluoro-benzyl (1R,cis,Z) 2,2-dimethyl -3-[3-oxo-3-tert.butoxy-1-propenyl]-cyclopropane-carboxylate A mixture of 310 g of (S)α-cyano-3-phenoxy-4-fluoro-benzyl alcohol, 310 g of (1R,cis,Z) 2,2-dimethyl-3-[3-oxo -3-tert.-butoxy-1-propenyl]-cyclopropane-carboxylic acid and 1.55 liters of methylene chloride was stirred until total dissolution occured and the mixture was cooled to −5° C. and mixed with a solution of 263.5 go dicyclohexylcarbodiimide, 3.1 g of 4-dimethylamino-pyridine and 530 ml of methylene chloride. The mixture was stirred at −5° C. for one hour and at room temperature for 3 hours and was vacuum filtered. The filtrate was washed with N hydrochloric acid and then with water, dried and evaporated to dryness under reduced pressure. The residue in 1.185 liters of isopropanol, 80 ml of water and 72 ml of triethylamine was stirred for 36 hours and was vacuum filtered. The product was washed with isopropanol to obtain 518 g of (S)α-cyano-3-phenoxy-4-fluoro-benzyl (1R,cis,Z) 2,2-dimethyl-3-[3-oxo-3-tert.-butoxy-1-propenyl]-cyclopropane-carboxylate melting at 114° C.

STEP B: (S)α-cyano-3-phenoxy-4-fluoro-benzyl (1R,cis,Z) 2,2-dimethyl-3-[3-oxo-3-hydroxy-1-propenyl]-cyclopropane-carboxylate A mixture of 350 g of the product of Step A, 35 g of p-toluene sulfonic acid and 3.5 liters of toluene was refluxed for 45 minutes and was then cooled, washed with water, dried and evaporated to dryness under reduced pressure to obtain 328 g of (S)α-cyano-3-phenoxy-4-fluoro-benzyl (1R,cis,Z) 2,2-dimethyl-3-[3-oxo-3-hydroxy-1-propenyl]-cyclopropane-carboxylate.

STEP C: (S)α-cyano-3-phenoxy-4-fluoro-benzyl (1R,cis,Z) 2,2-dimethyl-3-[3-oxo-3-(RS, 1,1,1-trifluoro-propyl-2-oxy)-1-propenyl]-cyclopropane-carboxylate 2.14 g of 1,1,1-trifluoro-isopropanol were added to a mixture of 2.05 g of the product of Step B in 10 ml of methylene chloride and then 50 mg of 4-dimethylaminopyridine and 1.3 g of dicyclohexylcarbodiimide were added thereto at 0° C. The mixture was stirred at 20° C. for 90 minutes and was filtered. The filtrate was evaporated to dryness under reduced pressure and the residue was added to 6 ml of a 9-1 cyclohexane-ethyl acetate mixture. The mixture was filtered and the filtrate was evaporated to dryness under reduced pressure. The residue was chromatographed over silica gel and was eluted with a 9-1 cyclohexane-ethyl acetate mixture to obtain 1.8 g of (S)α-cyano-3-phenoxy-4-fluoro-benzyl (1R,cis,Z) 2,2-dimethyl-3-[3-oxo-3-(RS, 1,1,1-trifluoro-propyl-2-oxy)-1-propenyl]-cyclopropane-carboxylate melting at 88° C. and having a specific rotation of $[\alpha]_D^{20} = +45°$ (c=0.5% in chloroform).

EXAMPLE 54

Using the procedure of Example 53, (S)α-cyano-3-phenoxy-4-fluoro-benzyl (1R,cis,Z) 2,2-dimethyl-3-[3-oxo-3-hydroxy-1-propenyl]-cyclopropane-carboxylate and 2,2,2-trifluoro-1-ethoxy-ethanol were reacted to obtain (S)α-cyano-3-phenoxy-4-fluoro-benzyl (1R,cis,Z) 2,2-dimethyl-3-[3-oxo-3(RS 2,2,2-trifluoro-1-ethoxy)-1-propenyl]-cyclopropane-carboxylate with a specific rotation of $[\alpha]_D^{20} = +37.5°$ (c=1% in chloroform).

EXAMPLE 55

(S)α-cyano-3-phenoxy-benzyl (1R,cis,Z) 2,2-dimethyl-3-[3-oxo-3-chloromethoxy-1-propenyl]-cyclopropane-carboxylate A solution of 18.5 g of (S)α-cyano-3-phenoxy-benzyl (1R,cis,Z) 2,2-dimethyl-3-[3-oxo-3-hydroxy-1-propenyl]-cyclopropane-carboxylate, 50 ml of methylene chloride and 50 ml of thionyl chloride was stirred at 20° to 25° C. for 2 hours and was then evaporated to dryness. The residue was admixed with 1.38 g of paraformaldehyde and 0.15 g of zinc chloride and the suspension was heated at 70° C. for 2½ hours. After treatment, the product was chromatographed over silica gel and eluted with an 8-2 hexane-ethyl acetate mixture to obtain (S)α-cyano-3-phenoxy-benzyl (1R,cis,Z) 2,2-dimethyl-3-[3-oxo-3-chloromethoxy-1-propenyl]-cyclopropane-carboxylate.

NMR Spectrum (deuterochloroform):

Peaks at 1.27-3 ppm (hydrogens of geminal methyls); at 5.9–6.1 ppm and 6.6–7 ppm (ethylenic hydrogens); at 5.8 ppm (hydrogens of —COO CH$_2$Cl).

EXAMPLE 56

(S)α-cyano-3-phenoxy-benzyl (1R,cis,Z) 2,2-dimethyl-3-[3-oxo-3-fluoromethoxy-1-propenyl]-cyclopropane-carboxylate Silver tetrafluoroboride (AgBF$_4$) was added at 0° to 5° C. to a solution of 6 g of the product of Example 55 in 60 ml of ether and the mixture was stirred at 0° C. for 30 minutes and at 20° C. for 90 minutes and was poured in aqueous sodium bicarbonate solution. The organic phase was washed with water and was chromatographed over silica gel. Elution with benzene yielded 1.95 g of (S)α-cyano-3-phenoxy-benzyl (1R,cis,Z) 2,2-dimethyl-3-[3-oxo-3-fluoromethoxy-1-propenyl]-cyclopropane-carboxylate.

NMR Spectrum (deuterochloroform):

Peaks at 1.27–1.3 ppm (hydrogens of geminal methyls); at 6.6–6.8 ppm (1'-hydrogen of ethylenic); at 5.9–6.1 ppm (2'-hydrogen of ethylenic); at 5.3 to 6.3 ppm (hydrogens of FCH$_2$O-).

EXAMPLE 57

Benzyl (1R,cis,Z) 2,2-dimethyl-3-[3-3-(2-fluoroethoxy)-1-propenyl]-cyclopropane-carboxylate STEP A: Benzyl (1R,cis,Z) 2,2-dimethyl-3-[3-3-tert.-butoxy-1-propenyl]-cyclopropane-carboxylate A solution of 25 g of (1R,cis,Z) 2,2-dimethyl-3-[3-oxo-3-tert.-butoxy-1-propenyl]-cyclopropane-carboxylic acid in 250 ml of tetrahydrofuran were added at 10° C. to a mixture of 2.6 g of sodium hydride in 100 ml of tetrahydrofuran and the mixture was stirred at 15° C. for 30 minutes. A solution of 35 ml of benzyl bromide in 100 ml of tetrahydrofuran was added to the mixture which was heated at 50° C. for 48 hours and then was cooled and poured into aqueous monosodium phosphate solution. The mixture was extracted with isopropyl ether and the organic phase was washed with water, dried and evaporated to dryness under reduced pressure. The residue was chromatographed over silica gel and was eluted with a 9-1 hexane-isopropyl ether mixture to obtain 30 g of benzyl (1R,cis,Z) 2,2-dimethyl-3-[3-oxo-3-tert.-butoxy-1-propenyl]-cyclopropane-carboxylate.

STEP B: Benzyl (1R,cis,Z) 2,2-dimethyl-3-[3-3-hydroxy-1-propenyl]-cyclopropane-carboxylate A mixture of 5 g of the product of Step A, 250 mg of p-toluene sulfonic acid and 30 ml of toluene was refluxed for one hour and was cooled and chromatographed over silica gel. Elution with a 1—1 hexane-ethyl acetate mixture containing 1% of acetic acid and crystallization from isopropyl ether yielded 3.05 g of benzyl (1R,cis,Z) 2,2-dimethyl-3-[3-oxo-3-hydroxy-1-propenyl]-cyclopropane-carboxylate melting at 69° C.

STEP C: Benzyl (1R,cis,Z) 2,2-dimethyl-3-[3-3-oxo-3-(2-fluoroethoxy)-1-propenyl]-cyclopropane-carboxylate Using the procedure of Example 48, 2-fluoro-ethanol and the product of Step A were reacted to obtain benzyl (1R,cis,Z) 2,2-dimethyl-3-[3-3-(2-fluoroethoxy)-1-propenyl]-cyclopropane-carboxylate with a specific rotation of $[\alpha_D^{20} = +53°$ (c=0.5% in chloroform).

EXAMPLE 58

Using the procedure of Example 53, difluoro-ethanol and the product of Step B of Example 57 were reacted to obtain benzyl (1R,cis,Z) 2,2-dimethyl-3-[3-3-(2,2-difluoroethoxy)-1-propenyl]-cyclopropane-carboxylate with a specific rotation of $[\alpha_D^{20} = +52°$ (c=0.2% in chloroform).

EXAMPLE 59

Using the procedure of Example 53, trifluoroethanol and the product of Step B of Example 57 were reacted to obtain benzyl (1R,cis,Z) 2,2-dimethyl-3-[3-3-(2,2,2-trifluoroethoxy)-1-propenyl]-cyclopropane-carboxylate with a specific rotation of $[\alpha_D^{20} = +45°$ (c=0.6% in chloroform).

EXAMPLE 60

(RS) 1-(6phenoxy-2-pyridyl)-ethyl (1R,cis,Z) 2,2-dimethyl-3-[3-oxo-3-1,1,1,3,3,3-hexafluoroisopropoxy)-1-propenyl]-cyclopropane-carboxylate STEP A: (RS) 1-(6-phenoxy-2-pyridyl)-ethyl (1R,cis,Z) 2,2-dimethyl-3-[3-oxo-3-tert.-butoxy-1-propenyl]-cyclopropane-carboxylate A solution of 55.7 g of dicyclohexylcarbodiimide, 2.6 g of 4-dimethylamino-pyridine and 450 ml of methylene chloride were added over 25 minutes at 0° C. to a mixture of 65 g of (1R,cis,Z) 2,2-dimethyl-3-[3-oxo-3-tert.-butoxy-1-propenyl]-cyclopropane-carboxylic acid, 70 g of (RS) 1-(6-phenoxy-2-pyridyl)-ethanol and 650 ml of methylene chloride and the mixture was stirred at 20° C. for 4 hours and was vacuum filtered. The filtrate was evaporated to dryness and the residue was chromatographed over silica gel. Elution with an 100-4 n-hexane-ethyl acetate mixture yielded 101 g of (RS) 1-(6-phenoxy-2-pyridyl)-ethyl (1R,cis,Z) 2,2-dimethyl-3-[3-oxo-3-tert.-butoxy-1-propenyl]-cyclopropane-carboxylate with a specific rotation of $[\alpha_D^{20} = +64°$ (c=1% in toluene).

STEP B: (RS) 1-(6-phenoxy-2-pyridyl)-ethyl (1R,cis,Z) 2,2-dimethyl-3-[3-oxo-3-hydroxy-1-propenyl]-cyclopropane-carboxylate A mixture of 5.649 g of the product of Step A, 0.5 g of p-toluene sulfonic acid and 70 ml of toluene was refluxed until gas evolution ceased and the mixture was cooled to 0° C. and filtered. The filtrate was evaporated to dryness under reduced pressure to obtain 4.741 g of (RS) 1-(6-phenoxy-2-pyridyl)-ethyl (1R,cis,Z) 2,2-dimethyl-3-[3-oxo-3-hydroxy-1-propenyl]-cyclopropane-carboxylate.

STEP C:

Using the procedure of Example 53, the product of Step B and 1,1,1,3,3,3-hexafluoroisopropanol were reacted to obtain (RS) 1-(6-phenoxy-2-pyridyl)-ethyl (1R,cis,Z) 2,2-dimethyl-3-[3-oxo-3-(1,1,1,3,3,3-hexafluoroisopropoxy)-1-propenyl]-cyclopropane-carboxylate with a specific rotation of $[\alpha_D^{20} = +55°$ (c=0.2% in chloroform).

EXAMPLE 61

(S)α-cyano-3-phenoxy-4-fluoro-benzyl (1R,cis,Z) 2,2-dimethyl-3-[3-oxo-3-(2,2,2-trifluoroethoxy)-1-propenyl]-cyclopropane-carboxylate STEP A: (RS)α-cyano-3-phenoxy-4-fluoro-benzyl (1R,cis,Z) 2,2-dimethyl-3-[3-oxo-3-tert.-butoxy-1-propenyl]-cyclopropane-carboxylate A solution of 30 g of (RS)α-cyano-3-phenoxy-4-fluoro-benzyl alcohol, 300 mg of 4-dimethylamino-pyridine and 50 ml of methylene chloride was added all at once at −5° C. to a solution of 30 g of (1R,cis,Z) 2,2-dimethyl-3-[3-oxo-3-tert.-butoxy-1-propenyl]-cyclopropane-carboxylic acid in 100 ml of methylene chloride and the mixture was stirred at 0° C. for 30 minutes and at 20° C. for 3 hours. The mixture was filtered and the filtrate was evaporated to dryness under reduced pressure. The residue was chromatographed over silica gel and was eluted with an 8-2 n-hexane-ethyl acetate mixture to obtain 53.9 g of (S)α-cyano-3-phenoxy-4-fluoro-benzyl (1R,cis,Z) 2,2-dimethyl-3-[3-oxo-3-tert.-butoxy-1-cyclopropane-carboxylate.

STEP B: (S)α-cyano-3-phenoxy-4-fluoro-benzyl (1R,cis,Z) 2,2-dimethyl-3-[3-oxo-3-tert.-butoxy-1-cyclopropane-carboxylate 53.9 g of the product of Step A were dissolved in 215 ml of isopropyl ether and the solution was seeded with a few crystals of the desired (S) ester. The mixture was stirred at 20° C. for 16 hours and was vacuum filtered to obtain 21.4 g of (S)α-cyano-3-phenoxy-4-fluoro-benzyl (1R,cis,Z) 2,2-dimethyl-3-[3-oxo-3-tert.-butoxy-1-cyclopropane-carboxylate melting at 114° C.

The mother liquors were evaporated to dryness under reduced pressure and the residue was added to a mixture of 74 ml of isopropanol, 5 ml of water and 4.5 ml of triethylamine. The mixture was stirred at room temperature for 20 hours and was vacuum filtered. The filtrate was evaporated to dryness and the residue was added again to a mixture of isopropanol, water and triethylamine and the procedure was repeated to obtain an additional 25 g of raw product which was crystallized from n-hexane to obtain 20.7 g of the desired ester melting at 114° C. for a total yield of 42.1 of product melting at 114° C.

STEP C: (S)α-cyano-3-phenoxy-4-fluoro-benzyl (1R,cis,Z)
2,2-dimethyl-3-[3-oxo-3-tert.-butoxy-1-cyclopropane-carboxylate.

1.6 g of p-toluene sulonic acid monohydrate were added to a solution of 16.4 g of the product of Step B in 160 ml of toluene and the mixture was refluxed until gas evolution ceased (about 30 minutes) and was cooled to 0° C. and filtered. The filtrate was evaporated to dryness under reduced pressure and the residue was chromatographed over silica gel. Elution with a 70-30-1 n-hexane-ethyl acetateacetic acid mixture yielded 13.3 g of (S)α-cyano-3-phenoxy-4-fluoro-benzyl (1R,cis,Z) 2,2-dimethyl-3-[3-oxo-3-hydroxy-1-propenyl]-cyclopropane-carboxylate melting at 99° C. and having a specific rotation of $[\alpha_D^{20} = +52.5° \pm 2.5°$ (c=0.5% in chloroform).

STEP D: (S)α-cyano-3-phenoxy-4-fluoro-benzyl (1R,cis,Z)
2,2-dimethyl-3-[3-oxo-3-chloro-1-propenyl]-cyclopropane-carboxylate 10 ml of thionyl chloride were added all at once at 20° C. to a solution of 4.5 g of the product of Step C in 20 ml of methylene chloride and the mixture was stirred for 105 minutes and was evaporated to dryness under reduced pressure to obtain 4.7 g of (S)α-cyano-3-phenoxy-4-fluorobenzyl (1R,cis,Z) 2,2-dimethyl-3-[3-oxo-3-chloro-1-propenyl]-cyclopropane-carboxylate.

STEP E: (S) α-cyano-3-phenoxy-4-fluoro-benzyl (1R,cis,Z)
2,2-dimethyl-3-[3-oxo-3-(2,2,2-trifluoroethoxy)-1-propenyl]-cyclopropane-carboxylate 2 ml of 2,2,2-trifluoroethanol were added at 20° C. to a solution of 2.14 g of the product of Step D in 8 ml of methylene chloride and the mixture was stirred for 90 minutes and was poured into aqueous monosodium phosphate solution. The decanted organic phase was washed with water, dried and evaporated to dryness under reduced pressure. The residue was chromatographed over silica gel and was eluted with a 1—1 cyclohexane-ethyl acetate mixture to obtain 2.33 g of (S)α-cyano-3-phenoxy-4-fluoro-benzyl (1R,cis,Z) 2,2-dimethyl-3-[3-oxo-3-(2,2,2-trifluoroethoxy)-1-propenyl]-cyclopropane-carboxylate melting at 56° C. and having a specific rotation of $[\alpha_D^{20} = +42° \pm 1°$ (c=1% in CHCl$_3$).

EXAMPLE 62

(S)α-cyano-3-phenoxy-4-fluoro-benzyl alcohol

A mixture of (RS)α-cyano-3-phenoxy-4-fluoro-benzyl alcohol, 100 ml of dichloromethane, 9.4 g of 1R,2S,5S, 6,6'2dimethyl-3-oxa-bicyclo-(3,1,0) hexan-2-ol and 0.1 g of p-toluene sulfonic acid was refluxed for 90 minutes and was poured into dilute aqueous potassium bicarbonate solution. The decanted organic phase was evaporated to dryness under reduced pressure to obtain 25.06 g of (1R,2R,5S) 6,6-dimethyl-3-oxa-2-[(RS)α-cyano-3-phenoxy-4-fluoro-benzyloxy]-bicyclo (3,1,0). The said product was chromatographed over silica gel and was eluted with a 8—2 hexane-ether mixture to obtain 8.85 g of (1R,2R,5S) 6,6-dimethyl-3-oxa-2-[(R)-α-cyano-3-phenoxy-4-fluoro-benzyl]-bicyclo (3,1,0) hexane melting at <50° C. and having a specific rotation of $[\alpha_D^{20} = +102°$(c=1% in benzene) and further chromatography resulted in 9.05 g of the corresponding (S) isomer melting at 65° C. and having a specific rotation of $[\alpha_D^{20} = +50°$ (c=0.4% in benzene).

Circular Dichroism (dioxane):

| (R) | isomer | max. at 279 nm | Δε = −0.27 |
| (S) | isomer | Inflex. towards 275 nm | Δε = +0.13 |
|     |        | max. at 281 nm | Δε = +0.15 |

NMR Spectrum (deuterochloroform):

(R) isomer: Peaks at 1.07 ppm (hydrogens of geminal methyls); at 1.33–1.78 ppm (hydrogens of cyclopropyl); at 3.7–4.1 ppm (hydrogens of —CH$_2$O—); at 5.2–5.5 ppm (hydrogen of

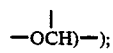

at 6.9–7.6 ppm (aromatic hydrogens).

(S) isomer: Peaks at 1.0 ppm (hydrogens of geminal methyls); at 1.55–1.57 ppm (hydrogens of cyclopropyl); at 3.8–3.9 ppm and 4.1–4.3 ppm (hydrogens of —CH$_2$O—); at 4.9–5.3 ppm (hydrogen of

at 6.9–7.6 ppm (aromatic hydrogens).

A mixture of 9 g of the (S) isomer, 100 ml of methanol and 90 mg of p-toluene sulfonic acid was stirred for 90 minutes at 20° C. and was then poured into water. The mixture was extracted with chloroform and the organic phase was evaporated to dryness under reduced pressure. The residue was chromatographed over silica gel and was eluted with a 7-3 hexane-ethyl acetate mixture containing 1% of acetic acid to obtain 4.9 g of (S)α-cyano-3-phenoxy-4-fluorobenzyl alcohol with a specific rotation of $[\alpha_D^{20} = +30°$ (c=0.5% in pyridine).

EXAMPLE 63

(3-propyn-2-yl-2,5-dioxo-imidazolidinyl)-methyl (1R,cis,Z)
2,2-dimethyl-3-[3-oxo-3-(1,1,1,3,3,3-hexafluoroisopropoxy)-1-propenyl]-cyclopropane-carboxylate STEP A:
(3-propyn-2-yl-2,5-dioxo-imidazolidinyl)-methyl (1R,cis,Z)
2,2-dimethyl-3-[3-oxo-3-hydroxy-1-propenyl)-cyclopropane-carboxylate 300 mg of p-toluene sulfonic acid monohydrate were added to a solution of 3.7 g of (3-propyn-2-yl-2,5-dioxo-imidazolidinyl-methyl (1R,cis,Z) 2,2-dimethyl-3-[3-oxo-3-tert.-butoxy-1-propenyl]-cyclopropane-carboxylate in 35 ml of toluene and the mixture was refluxed until gas evolution of isobutylene ceased (about 25 minutes). The mixture was cooled and filtered and the filtrate was evaporated to dryness under reduced pressure. The residue was chomatographed over silica gel and was eluted with a 60-40-1 n-hexane-ethyl acetate-acetic acid mixture to obtain 3.1 g of (3-propyn-2-yl-2,5-dioxo-imidazolidinyl)-methyl (1R,cis,Z) 2,2-dimethyl-3-[3-oxo-3-hydroxy-1-propenyl]-cyclopropane-carboxylate with a specific rotation of $[\alpha_D^{20} = +16°$ (c=0.25% in CHCl$_3$).

STEP B:
(3-propyn-2-yl-2,5-dioxo-imidazolidinyl)-methyl (1R,cis,Z) 2,2-dimethyl-3-[3-oxo-(1,1,1,3,3,3-hexafluoroisopropoxy)-1-propenyl]-cyclopropane-carboxylate 1.2 ml of hexafluoroisopropanol were added to a solution of 1.39 g of the product of Step A in 10 ml of methylene chloride and then a solution of 1.0 g of dicyclohexylcarbodiimide, 30 mg of 4-dimethylamino-pyridine and 5 ml of methylene chloride were added at 5° C. to the mixture. The mixture was stirred at 5° C. for 10 minutes, at 20° C. for 3 hours and was filtered. The filtrate was evaporated to dryness under reduced pressure and the residue was chromatographed over silica gel. Elution with a 7-3 n-hexane-ethyl acetate mixture yielded 1.6 g of (3-propyn-2-yl-2,5-dioxo-imidazolidinyl)-methyl (1R,cis,Z) 2,2-dimethyl-3-[3-oxo-(1,1,1,3,3,3-hexafluoroisopropoxy)-1-propenyl]-cyclopropane-carboxylate with a specific rotation of $[\alpha_D^{20} = +16° \pm 16°$ (c=0.5% in benzene).

EXAMPLE 64

(3-propyn-2-yl-2,5-dioxo-imidazolidinyl)-methyl (1R,cis,Z) 2,2-dimethyl-3-[3-oxo-(1,1,1,3,3,3-hexafluoroisopropoxy)-1-propenyl]-cyclopropane-carboxylate 400 mg of p-toluene sulfonic acid monohydrate were added in 4 portions over 2 hours to a mixture of 700 mg of (3-propyn-2-yl-2,5-dioxo-imidazolidinyl)-methyl (1R,cis,Z) 2,2-dimethyl-3-[3-oxo-3-methoxy-1-propenyl]-cyclopropane-carboxylate, 3.5 ml of dioxane and 1 ml of water and the mixture was refluxed for 7 hours and was stirred at 20° C. for 16 hours. The solvent was distilled under reduced pressure and methylene chloride was added to the residue. The organic phase was washed with water, dried and evaporated to dryness under reduced pressure. The residue was chromatographed over silica gel and was eluted with a 60-40-1 n-hexane-ethyl acetate-acetic acid mixture to obtain 200 mg of (3-propyn-2-yl-2,5-dioxo-imidazolidinyl)-methyl (1R,cis,Z) 2,2-dimethyl-3-[3-oxo-3-hydroxy-1-propenyl]-cyclopropane-carboxylate identical to the product of Step A of Example 63. The said product was treated as in Step B of Example 63 to obtain (3-propyn-2-yl-2,5-dioxo-imidazolidinyl)-methyl (1R,cis,Z) 2,2-dimethyl-3-[3-oxo-3-(1,1,1,3,3,3-hexafluoroisopropoxy)-1-propenyl]-cyclopropane-carboxylate.

EXAMPLE 65

A soluble concentrate was prepared by homogenously mixing 0.25 g of the product of Example 1 or Example 51 (isomer A), 1 g of piperonyl butoxide, 0.25 g of Tween 80, 0.1 g of Topanol A and 98.4 g of water.

An emulsifiable concentrate was prepared by intimately mixing 0.015 g of the product of Example 1 or isomer B of Example 51, 0.5 g of piperonyl butoxide, 0.1 g of Topanol A, 3.5 g of Tween 80 and 95.885 of xylene.

A second emulsifiable concentrate was prepared by homogenously mixing 1.5 g of the product of Example 1 or Example 48, 20 g of Tween 80, 0.1 g of Topanol A and 78.4 g of xylene.

A fumigant composition was prepared by homogenously mixing 0.25 g of the product of Example 1 or Example 50, 25 g of tabu powder, 40 g of cedar needle powder, 33.75 g of pine wood powder, 0.5 g of brilliant green and 0.5 g of p-nitrophenol.

PARASITIC STUDY

A. Lethal effect on houseflies

The test insects were female houseflies of strain sensitive to pyrethrinoids, bred at 22°–23° C. and 60 to 65% relative humidity and 4 to 5 days old. One µl of an acetone solution of the test compound was topically applied to the dorsal thorax of the insects with an Arnold micro-manipulator using 50 insects for each dose. The number of dead was determined 24 hours later and the compounds of Examples 1, 23 and 29, isomer A and B of Example 51 and Example 61 had a DL$_{50}$ of 1.115, 0.962, 0.825, 0.50, 0.54 and 0.30 ng per individual, respectively.

B. Lethal effect on larvae of Spodoptera littoralis

The test was effected by a topical application of an acetone solution of the test compound with an Arnold micromanipulator to the dorsal thorax of larvae of Spodoptera littoralis in the 4th larvae stage using 15 insects per dose. The larvae were 10 days old having been kept at 24° C. and a 65% relative humidity and the larvae, after treatment, were placed in an artifical nutritive medium (Poitout media) and the number of dead was determined after 48 hours. The compounds of Examples1, 35, isomer A and B of Example 51 and Example 61 had a DL$_{50}$ of 4.699, 0.544, 9.0, 8.46 and 2.2 ng per individual, respectively.

C. Knock-down power against houseflies 50 female houseflies 4 to 5 days old per dose were subjected to a direct spray in a Kearns and March cylinder using as the solvent a mixture in equal volumes of acetone and Isopar L (amount of solution used 2×0.2 cm3). About 50 individuals per dose of treatment are used. Readings were taken every minute for 10 minutes and then at 15 minutes to determine the KT$_{50}$ by the usual method. The results are reported in Table I.

TABLE I

| Product of Example | KT$_{50}$ in min. | Concentration g/l |
|---|---|---|
| 1 | 3.534 | 1 |
| 2 | 3.608 | 0.25 |
| 26 | 1.550 | 0.25 |
| 30 | 3.498 | 1 |
| 35 | 2.894 | 1 |

The said test was repeated using 0.25 g/l of the test compound in a mixture of 95% of Isopar L and 5% of acetic acid and the results are reported in Table II.

TABLE II

| Product of Example | KT$_{50}$ in min. |
|---|---|
| 49 | 2.89 |
| 50 | 3.93 |
| 52 | 5.30 |
| 55 | 2.17 |
| 56 | 4.90 |
| 62 | 0.61 |

D. Activity against Tetranychus Urticae

Bean plants comprising 2 cotyledonous leaves were treated by a Fisher pistol with an acetonic solution of the product. After drying, 25 females of the acarien Tetranychus Urticae are deposited per leaf, that is 50 individuals per dose per plant. The number of living and dead acariens were determined after 1, 24, 48 and 72 hours. The product Example 1 showed a good adulticidal activity of 2.8 mg/l. The A and B isomers of Example 51 and 61 show an $CL_{50}$ activity of 676, 501 and 1022 mg/hl, respectively.

E. Activity against Germanic beetles

Tests with the compound of Example 1 were carried out on Blatella germanic beetles with an acetone solution a predetermined concentration of the compound being place a Petri dish with a 20 cm diameter. After evaporation of the acetone, 26 male beetles per test concentration were placed in the Petri dish for one hour and the insects were then placed in healthly surroundings. The number of dead beetles was determined after 24 hours, 48 hours and 3 and 5 days and lethal concentration at which 50% of the beetles ($CL_{50}$) were dead was determined to be 0.216 mg/m². The results of the same test showed a $CL_{50}$ activity of 1.92, 0.07, 0.122 and 0.095 mg/m² for the compounds of Examples 48, isomers A and B of Example 51 and 61 respectively. The compounds of Examples 63 and 64 had a $CL_{50}$ greater than 10 mg/m².

F. Lethal activity against Aphis Cracivora 10 seven days old adult Aphis Cracivora were used for each test concentration of the contact-ingestion method. A Fischer pistol was used to spray a bean leaf placed in a plastic Petri dish with a circle of damp paper with 2 ml of a 1—1 acetone-water mixture of the test product. One ml was applied to each side of the leaf which was dried and infested with the insects. The mortality was determined after 24 hours and compared with an untreated control. The $CL_{50}$ was 3.1, 0.2, 6.3, 5.8 and 3.4 mg/l for the compounds of Examples 60, 54, isomers A and B of 51 and 61 respectively.

G. Lethal activity against Acanthoscelides Obtectus

The test used was the same as that for Spodoptera larvae using larvae in the second last stage and after treatment, the larvae were fed with bean plants. The degree of mortality was determined 72 hours after treatment and the product of Example 61 had a $DL_{50}$ of 5.7 mg per individual.

CONCLUSION

The test results show that the compounds of the invention have a good insecticidal and acaricidal activity.

Various modifications of the compounds and methods of the invention may be made without departing from the spirit or scope thereof and it is to be understood that the invention is intended to be limited only as defined in the appended claims.

What is claimed is:

1. A compound selected from the group consisting of (1,3,4,5,6,7-hexahydro-1,3-dioxo-2H-isoindol-2-yl)-methyl (1R,cis, ΔZ) 2,2-dimethyl-3-[3-oxo-3-(2,2,2-trifluoroethoxy)-1-propenyl]-cyclopropane carboxylate, (1,3,4,5,6,7-hexahydro-1,3-dioxo-2H-isoindol-2-yl)-methyl (1R, cis, ΔZ) 2,2-dimethyl-3-[3-oxo-3-(2,2,2-trifluoro-1-(trifluoromethyl)-ethoxy-1-propenyl] cyclopropane carboxylate, (1,3,4,5,6,7-hexahydro-1,3-dioxo-2H-isoindol-2-yl)-methyl (1R, cis, ΔZ) 2,2-dimethyl-3-[3-oxo-3-cyclopropylmethoxy-1-propenyl]-cyclopropane carboxylate, (1,3,4,5,6,7-hexahydro-1,3-dioxo-2H-isoindol-2-yl)-methyl (1R, cis, ΔZ) 2,2-dimethyl-3-[3-oxo-3-propoxy-1-propenyl]-cyclopropane carboxylate, (1,3,4,5,6,7-hexahydro-1,3-dioxo-2H-isoindol-2-yl)-methyl (1R, cis, ΔZ) 2,2-dimethyl-3-[3-oxo-3-(1-methylethoxy)-1-propenyl]-cyclopropane carboxylate and (1,3,4,5,6,7-hexahydro-1,3-dioxo-2H-isoindol-2-yl)-methyl (1R, cis, ΔZ) 2,2-dimethyl-3-[3-oxo-3-methoxy-1-propenyl]-cyclopropane carboxylate.

2. A composition for combatting an infection caused by acariens in warm-blooded animals comprising an anti-acaricidally effective amount of a compound of claim 1 and a carrier.

3. A method of combatting an infection caused by acariens in warm-blooded animals comprising contacting warm-blooded animals with an anti-acaricidally effective amount of a compound of claim 1.

* * * * *

UNITED STATES PATENT AND TRADEMARK OFFICE
CERTIFICATE OF CORRECTION

PATENT NO. : 4,883,806

DATED : Nov. 28, 1989

Page 1 of 4

INVENTOR(S) : Jacques Martel, Jean Tessier and Andre Teche

It is certified that error appears in the above-identified patent and that said Letters Patent is hereby corrected as shown below:

| Col. | Line | | |
|---|---|---|---|
| [75] | Inventors | "Andre Teche" should be --Andre Teche-- | |
| [57] | Abstract | "-$CF_3$,4" should be -- -$CF_3$, 3,4-- | |
| 2 | Formula 3 | 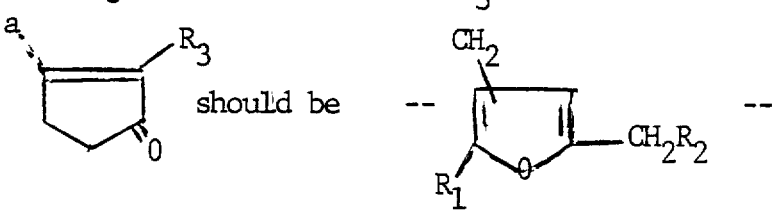 | |
| 2 | 7 | "wherein R" should be --wherein $R_1$-- | |
| 4 | 27&28 | "-CH-" should be --$CH_2$- -- (with 2 subscript) | |
| 5 | 34&35 | -CH- should be --$CH_2$- -- (with 2 subscript) | |
| 6 | 8 & 9 | "-$CH_2$-CH-" should be -- -$CH_2$-$CH_2$ -- (with 2 subscript) | |
| 6 | 17&18 | --"-CH- should be -- -$CH_2$-- (with 2 subscript) | |
| 6 | 32 | $(CH_2)_n$-CH-$CH_2$ with O O bridged to C($CH_3$)($CH_3$) should be -- -$CH_2$-CH-$CH_2$ with O O bridged to C($CH_3$)($CH_3$) -- | |

UNITED STATES PATENT AND TRADEMARK OFFICE
CERTIFICATE OF CORRECTION

PATENT NO. : 4,883,806

DATED : Nov. 28, 1989

INVENTOR(S) : Jacques Martel, Jean Tessier and Andre Teche

It is certified that error appears in the above-identified patent and that said Letters Patent is hereby corrected as shown below:

| Col. | Line | |
|---|---|---|
| 7 | 35 | 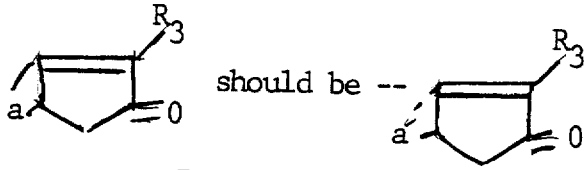 |
| 7 | 40 | 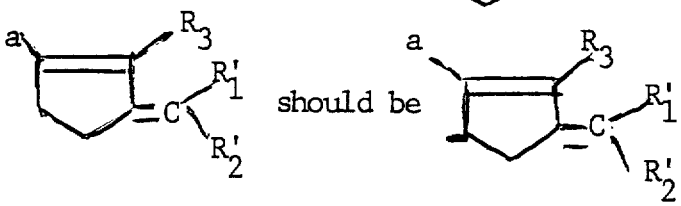 |
| 8 | 30&31 | "6σ-ethynyl" should be -- α -ethynyl-- |
| 12 | 19 | "lea" should be --lead-- |
| 13 | 11 | "(1R,cis,α Z)" should be --(1R,cis ,Δ Z) -- |
| 13 | 14 | " " " " " " " " " " " " " " " " " " |
| 13 | 17 | " " " " " " " " " " " " " " " " " " |
| 16 | 27 | "70-20-1" should be --70-30-1-- |
| 16 | 30 | "propenyl]cyclopropane" should be --propenyl]-cyclopropane-- |
| 17 | 43 | "Step A" should be on next line |
| 24 | 55 | "COO-$\underline{CH}_2$-CH$_2$-O)" should be --COO-$\underline{CH}_2$-CH$_2$-O)-- |
| 24 | 56&57 | " " " " " " " " " " " " " " " " " " " |
| 22 | 68 | "$[\alpha_D^{20}$" should be --$[\alpha]_D^{20}$ -- |
| 27 | 43 | "3oxo-3-" should be -- 3-oxo-3- -- |
| 29 | 25 | "Step B" should start a new paragraph |

UNITED STATES PATENT AND TRADEMARK OFFICE
CERTIFICATE OF CORRECTION

PATENT NO. : 4,883,806

DATED : Nov. 28, 1989

INVENTOR(S) : Jacques Martel, Jean Tessier and André Têche

It is certified that error appears in the above-identified patent and that said Letters Patent is hereby corrected as shown below:

| Col. | Line | |
|---|---|---|
| #30 | 19 | See Amendment dated Feb. 27, 1989 "phenoxy" should be --propoxy-- |
| 30 | 25 | " " " " " " " " " " " " " " " " " " " " " |
| 30 | 55&56 | "Example 27" should be in the middle |
| 36 | 30 | "cyclohexaneethyl" should be --cyclohexane-ethyl-- |
| 38 | 26 | ">40°" should be --<40°C-- |
| 39 | 17&18 | "263.5 g°" should be --263.5 g of |
| 41 | 30 | "$[\alpha_D^{20}$" should be --$[\alpha]_D^{20}$ |
| 41 | 36 | " " " " " " " " " " " " " |
| 41 | 45 | " " " " " " " " " " " " " |
| 42 | 1 | " " " " " " " " " " " " " |
| 42 | 22 | " " " " " " " " " " " " " |
| 43 | 20 | " " " " " " " " " " " " " |
| 43 | 50 | " " " " " " " " " " " " " |
| 43 | 58 | "6,6'2dimethyl" should be --6,6-dimethyl-- |
| 44 | 2 | "$[\alpha_D^{20}$" should be --$[\alpha]_D^{20}$ |
| 44 | 5 | " " " " " " " " " " " " " |
| 44 | 26&27 | "-CH$_2$0)" should be --CH$_2$0-)-- |
| 44 | 44 | "$[\alpha_D^{20} = +30°$" should be --$[\alpha]_D^{20} = -30°$-- |

UNITED STATES PATENT AND TRADEMARK OFFICE
CERTIFICATE OF CORRECTION

PATENT NO. : 4,883,806
DATED : Nov. 28, 1989
INVENTOR(S) : Jacques Martel, Jean Tessier and Andre Teche It is certified that error appears in the above-identified patent and that said Letters Patent is hereby corrected as shown below:

| Col. | Line | |
|------|------|---|
| 45 | 1 | "$[\alpha]_D^{20}$" should be --$[\alpha]_D^{20}$-- |
| 45 | 23 | "  "  "  "  "  "  "  "  "  "  "  " |
| 24 | 55 | "4.3" should be --4.38--. |

Signed and Sealed this

Fifth Day of November, 1991

Attest:

HARRY F. MANBECK, JR.

Attesting Officer

Commissioner of Patents and Trademarks